US007418966B2

(12) United States Patent
Faries, Jr. et al.

(10) Patent No.: US 7,418,966 B2
(45) Date of Patent: *Sep. 2, 2008

(54) SURGICAL DRAPE AND METHOD OF DETECTING FLUID AND LEAKS IN THERMAL TREATMENT SYSTEM BASINS

(75) Inventors: Durward I. Faries, Jr., Las Vegas, NV (US); Bruce R. Heymann, Vienna, VA (US); David Hendrix, Ashburn, VA (US)

(73) Assignee: O. R. Solutions, Inc., Chantilly, VA (US)

( * ) Notice: Subject to any disclaimer, the term of this patent is extended or adjusted under 35 U.S.C. 154(b) by 635 days.

This patent is subject to a terminal disclaimer.

(21) Appl. No.: 10/836,198

(22) Filed: May 3, 2004

(65) Prior Publication Data

US 2004/0200483 A1 Oct. 14, 2004

Related U.S. Application Data

(63) Continuation-in-part of application No. 10/372,674, filed on Feb. 25, 2003, now Pat. No. 6,910,485, which is a continuation-in-part of application No. 09/983,021, filed on Oct. 22, 2001, now Pat. No. 6,810,881, application No. 10/836,198.

(60) Provisional application No. 60/467,130, filed on May 2, 2003.

(51) Int. Cl.
*A61B 19/00* (2006.01)
*A61F 7/00* (2006.01)

(52) U.S. Cl. .......................... 128/849; 128/850; 128/851; 128/852; 128/853; 128/854; 128/855; 128/856; 219/430; 219/438

(58) Field of Classification Search .......... 128/849–856, 128/846; 62/66; 4/580, 655, 585; D24/187; 219/494, 212, 217; 392/308
See application file for complete search history.

(56) References Cited

U.S. PATENT DOCUMENTS 2,613,511 A 10/1952 Walsh
3,869,596 A 3/1975 Howie (Continued)

FOREIGN PATENT DOCUMENTS

JP 61-185967 11/1986
JP 06-123532 5/1994

OTHER PUBLICATIONS

"Electrically Conductive Polymer Film"; Creative Materials Incorporated; www.creativematerials.com; 1 page.
Pique, A., et al.; "Processing of Functional Polymers and Organic Thin Films by the Matrix-Assisted Pulsed Laser Evaporation (MAPLE) Technique"; Applied Surface Science, vol. 186, 2002; pp. 408-415.

(Continued)

*Primary Examiner*—Patricia Bianco
*Assistant Examiner*—Tarla Patel
(74) *Attorney, Agent, or Firm*—Edell, Shapiro & Finnan, LLC

(57) ABSTRACT

A drape according to the present invention is constructed of or includes conductive and insulating drape segments and is disposed over a top surface of a thermal treatment system having a basin recessed therein. A portion of the drape is pushed down into, and conforms to, the basin to form a drape container or receptacle within the basin for collecting a sterile medium. The conductive segments provide a signal indicating the presence of liquid and/or leaks within the drape container to the system to facilitate control of system operation. In addition, a drape utilized for a plural basin thermal treatment system may form a drape receptacle within each basin. Each drape receptacle includes conductive and insulating drape segments to detect the presence of liquid and/or a leak within that drape receptacle. The conductive segments of the drape receptacles provide signals to the system to facilitate control of system operation.

51 Claims, 6 Drawing Sheets

U.S. PATENT DOCUMENTS

| | | | |
|---|---|---|---|
| 3,902,484 A | 9/1975 | Winters | |
| 4,270,067 A | 5/1981 | Thomas et al. | |
| 4,284,880 A | 8/1981 | Keiser | |
| 4,393,659 A | 7/1983 | Keyes et al. | |
| 4,458,139 A | 7/1984 | McClean | |
| 4,474,016 A | 10/1984 | Winchell | |
| 4,522,041 A | 6/1985 | Menzel | |
| 4,625,098 A | 11/1986 | Joe | |
| 4,782,835 A | 11/1988 | Bernardini | |
| 4,828,876 A | 5/1989 | Ohhara et al. | |
| 4,869,271 A | 9/1989 | Idris | |
| 4,903,710 A | 2/1990 | Jessamine et al. | |
| 4,934,152 A | 6/1990 | Templeton | |
| 4,967,061 A | 10/1990 | Weber, Jr. et al. | |
| 5,040,699 A | 8/1991 | Gangemi | |
| 5,042,455 A | 8/1991 | Yue et al. | |
| 5,042,981 A | 8/1991 | Gross | |
| 5,129,033 A | 7/1992 | Ferrara et al. | |
| 5,163,299 A | 11/1992 | Faries, Jr. et al. | |
| 5,174,306 A | 12/1992 | Marshall | |
| 5,310,524 A | 5/1994 | Campbell et al. | |
| 5,331,820 A | 7/1994 | Faries, Jr. et al. | |
| 5,333,326 A | 8/1994 | Faries, Jr. et al. | |
| 5,345,063 A | 9/1994 | Reusche et al. | |
| 5,363,746 A | 11/1994 | Gordon | |
| 5,374,813 A | 12/1994 | Shipp | |
| 5,383,476 A | 1/1995 | Peimer et al. | |
| 5,386,835 A | 2/1995 | Elphick et al. | |
| 5,396,905 A | 3/1995 | Newman et al. | |
| 5,400,267 A | 3/1995 | Denen et al. | |
| 5,400,616 A | 3/1995 | Faries, Jr. et al. | |
| 5,402,644 A | 4/1995 | Faries, Jr. et al. | |
| 5,429,801 A | 7/1995 | Faries, Jr. et al. | |
| 5,435,322 A | 7/1995 | Marshall | |
| 5,443,082 A | 8/1995 | Mewburn | |
| 5,449,892 A | 9/1995 | Yamada | |
| 5,457,962 A | 10/1995 | Faries, Jr. et al. | |
| 5,463,213 A | 10/1995 | Honda | |
| 5,502,980 A | 4/1996 | Faries, Jr. et al. | |
| 5,517,170 A | 5/1996 | Peters et al. | |
| 5,522,095 A | 6/1996 | Faries, Jr. et al. | |
| 5,522,805 A | 6/1996 | Vancaillie et al. | |
| 5,524,478 A | 6/1996 | Joy et al. | |
| 5,524,643 A | 6/1996 | Faries, Jr. et al. | |
| 5,531,697 A | 7/1996 | Olsen | |
| 5,539,185 A | 7/1996 | Polster | |
| 5,551,240 A | 9/1996 | Faries, Jr. et al. | |
| 5,615,423 A | 4/1997 | Faries, Jr. et al. | |
| 5,653,938 A | 8/1997 | Faries, Jr. et al. | |
| 5,658,478 A | 8/1997 | Roeschel et al. | |
| 5,664,582 A | 9/1997 | Szymaitiz | |
| 5,717,188 A | 2/1998 | Vaillancourt | |
| 5,800,352 A | 9/1998 | Ferre et al. | |
| 5,809,788 A | 9/1998 | Faries, Jr. et al. | |
| 5,816,252 A | 10/1998 | Faries, Jr. et al. | |
| 5,857,467 A | 1/1999 | Faries, Jr. et al. | |
| 5,862,672 A | 1/1999 | Faries, Jr. et al. | |
| 5,879,621 A | 3/1999 | Faries, Jr. et al. | |
| 5,950,438 A | 9/1999 | Faries, Jr. et al. | |
| 6,003,328 A | 12/1999 | Faries, Jr. et al. | |
| 6,035,855 A | 3/2000 | Faries, Jr. et al. | |
| 6,087,636 A | 7/2000 | Faries, Jr. et al. | |
| 6,091,058 A * | 7/2000 | Faries et al. | 219/430 |
| 6,102,044 A | 8/2000 | Naidyhorski | |
| 6,255,627 B1 | 7/2001 | Faries, Jr. et al. | |
| 6,371,121 B1 | 4/2002 | Faries, Jr. et al. | |
| 6,524,742 B1 | 2/2003 | Emanuel et al. | |
| 6,586,950 B1 | 7/2003 | Sargent et al. | |
| 6,810,881 B2 * | 11/2004 | Faries et al. | 128/849 |
| 6,860,271 B2 | 3/2005 | Faries, Jr. et al. | |
| 6,910,485 B2 | 6/2005 | Faries, Jr. et al. | |
| 6,918,395 B2 | 7/2005 | Faries, Jr. et al. | |
| 7,041,941 B2 | 5/2006 | Faries, Jr. et al. | |
| 7,176,030 B2 | 2/2007 | Faries, Jr. et al. | |
| 7,276,675 B2 | 10/2007 | Faries, Jr. et al. | |
| 7,307,245 B2 | 12/2007 | Faries, Jr. et al. | |
| 7,347,210 B2 | 3/2008 | Faries, Jr. et al. | |
| 7,350,373 B1 | 4/2008 | Faries, Jr. et al. | |
| 2003/0231900 A1 | 12/2003 | Faries, Jr. et al. | |
| 2004/0200480 A1 * | 10/2004 | Faries et al. | 128/849 |
| 2004/0200483 A1 | 10/2004 | Faries, Jr. et al. | |
| 2004/0208780 A1 * | 10/2004 | Faries et al. | 422/3 |
| 2005/0247169 A1 | 11/2005 | Faries, Jr. et al. | |
| 2006/0065276 A1 | 3/2006 | Kammer et al. | |
| 2006/0086361 A1 | 4/2006 | Kammer et al. | |
| 2006/0091128 A1 | 5/2006 | Kammer et al. | |
| 2006/0194324 A1 | 8/2006 | Faries, Jr. et al. | |
| 2006/0260443 A1 | 11/2006 | Faries, Jr. et al. | |
| 2007/0089753 A1 | 4/2007 | Faries, Jr. et al. | |

OTHER PUBLICATIONS

"Electrically Conductive Polymer Nanocomposite Materials"; retrieved from Internet Apr. 24, 2003; www.afrlhorizons.com/Briefs/Sept02/ML0206.html; 2 pages.

* cited by examiner

SURGICAL DRAPE AND METHOD OF DETECTING FLUID AND LEAKS IN THERMAL TREATMENT SYSTEM BASINS

CROSS-REFERENCE TO RELATED APPLICATIONS

This application is a continuation-in-part of U.S. patent application Ser. No. 10/372,674, entitled "Medical Solution Thermal Treatment System and Method of Controlling System Operation in Accordance with Detection of Solution and Leaks in Surgical Drape Containers" and filed Feb. 25, 2003, now U.S. Pat. No. 6,910,485 which is a continuation-in-part of U.S. patent application Ser. No. 09/983,021, entitled "Medical Solution Thermal Treatment System and Method of Controlling System Operation in Accordance with Detection of Solution and Leaks in Surgical Drape Containers" and filed Oct. 22, 2001 now U.S. Pat. No. 6,810,881. In addition, the present application claims priority from U.S. Provisional Patent Application Ser. No. 60/467,130, entitled "Surgical Drape and Method of Detecting Fluid and Leaks in Thermal Treatment System Basins" and filed May 2, 2003. The disclosures of the aforementioned patent applications are incorporated herein by reference in their entireties.

BACKGROUND OF THE INVENTION

1. Technical Field

The present invention pertains to surgical drapes. In particular, the present invention pertains to a surgical drape to contain a sterile surgical solution and facilitate detection of the presence of solution and/or leaks within a thermal treatment system basin. The surgical drape is preferably utilized with thermal treatment systems that thermally treat a sterile surgical liquid, such as the types disclosed in U.S. Pat. No. 4,393,659 (Keyes et al.), U.S. Pat. No. 4,934,152 (Templeton), U.S. Pat. No. 5,163,299 (Faries, Jr. et al.), U.S. Pat. No. 5,331,820 (Faries, Jr. et al.), U.S. Pat. No. 5,333,326 (Faries, Jr. et al.), U.S. Pat. No. 5,400,616 (Faries, Jr. et al.), U.S. Pat. No. 5,402,644 (Faries, Jr. et al.), U.S. Pat. No. 5,429,801 (Faries Jr. et al.), U.S. Pat. No. 5,457,962 (Faries, Jr. et al.), U.S. Pat. No. 5,502,980 (Faries, Jr. et al.), U.S. Pat. No. 5,522,095 (Faries, Jr. et al.), U.S. Pat. No. 5,524,643 (Faries, Jr. et al.), U.S. Pat. No. 5,551,240 (Faries, Jr. et al.), U.S. Pat. No. 5,615,423 (Faries, Jr. et al.), U.S. Pat. No. 5,653,938 (Faries, Jr. et al.), U.S. Pat. No. 5,809,788 (Faries, Jr. et al.), U.S. Pat. No. 5,816,252 (Faries, Jr. et al.), U.S. Pat. No. 5,857,467 (Faries, Jr. et al.), U.S. Pat. No. 5,862,672 (Faries, Jr. et al.), U.S. Pat. No. 5,879,621 (Faries, Jr. et al.), U.S. Pat. No. 5,950,438 (Faries, Jr. et al.), U.S. Pat. No. 6,003,328 (Faries, Jr. et al.), U.S. Pat. No. 6,035,855 (Faries, Jr. et al.), U.S. Pat. No. 6,087,636 (Faries, Jr. et al.), U.S. Pat. No. 6,091,058 (Faries, Jr. et al.), U.S. Pat. No. 6,255,627 (Faries, Jr. et al.) and U.S. Pat. No. 6,371,121 (Faries, Jr. et al.) and U.S. patent application Publication No. 2003/0231990 (Faries, Jr. et al.). The disclosures in the above-mentioned patents and patent application publication are incorporated herein by reference in their entireties.

2. Discussion of the Related Art

The above-referenced Keyes et al. U.S. Pat. No. 4,393,659 discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton U.S. Pat. No. 4,934,152, the Keyes et al. system has a number of disadvantages. In particular, the separate product basin must be removed and re-sterilized after each use. Additionally, the glycol or other thermal transfer medium is highly flammable or toxic and, in any event, complicates the procedure. The Templeton U.S. Pat. No. 4,934,152 discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al. U.S. Pat. No. 5,163,299 notes that scraping congealed liquid from the drape is undesirable in view of the potential for damage to the drape, resulting in a compromise of sterile conditions. As a solution to the problem, the Faries, Jr. et al. U.S. Pat. No. 5,163,299 proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel. Accordingly, several of the Faries, Jr. et al. (e.g., U.S. Pat. Nos. 5,331,820; 5,400,616; 5,457,962; 5,502,980; 5,653,938; 5,809,788; 5,857,467; 5,950,438; 6,003,328; and 6,035,855) resolve the problem of manual drape manipulation by disclosing various techniques and/or dislodgment mechanisms to automatically remove the congealed liquid adhering to the drape without endangering the integrity of the drape.

The Templeton U.S. Pat. No. 4,934,152 further discloses an electrical heater disposed at the bottom of the basin to convert the sterile slush to warmed liquid, or to heat additional sterile liquid added to the basin. Templeton describes the need for such warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both warmed sterile liquid and sterile surgical slush. Accordingly, several of the Faries, Jr. et al. (e.g., U.S. Pat. Nos. 5,333,326; 5,429,801; 5,522,095; 5,524,643; 5,615,423; 5,653,938; 5,816,252; 5,862,672; 5,857,467; 5,879,621; 6,091,058; and 6,255,627) disclose a manner in which to simultaneously provide both surgical slush and warmed surgical liquid during a surgical procedure by utilizing a machine having plural basins with each basin either producing surgical slush or heating a sterile liquid. This machine typically utilizes a single surgical drape that forms a drape receptacle within each basin to collect sterile slush and heated sterile liquid produced by the machine in the respective basins.

In addition, several of the drapes and thermal treatment systems disclosed in the above-mentioned patents include specialized features to enhance various aspects of thermal treatment system operation. For example, some of the specialized features may include: bladder drapes (e.g., as disclosed in U.S. Pat. Nos. 5,809,788; 5,950,438; and 6,003,328); drapes having plates or disks (e.g., as disclosed in U.S. Pat. Nos. 5,457,962 and 5,502,980); reinforced drapes (e.g., as disclosed in U.S. Pat. No. 5,857,467); drape indicators and corresponding thermal treatment system detection devices to ensure sterility by enabling system operation in response to detecting a sterile drape placed on the system (e.g., as disclosed in U.S. Pat. Nos. 5,653,938 and 5,879,621); drapes having indicia to direct placement of the drapes on thermal treatment systems (e.g., as disclosed in U.S. Pat. No. 5,615,423); surgical drapes constructed of materials having a coefficient of friction in a particular range and/or drapes including attachment mechanisms such that a drape may withstand being drawn under a dislodgment mechanism (e.g., as disclosed in U.S. Pat. No. 6,035,855); a stand to elevate objects within a heated basin above the basin floor (e.g., as disclosed in U.S. Pat. No. 6,087,636) and/or a heater configured to cover a portion of the basin (e.g., as disclosed in U.S. Pat. Nos. 6,091,058 and 6,255,627) to prevent the drape from overheating and puncturing when objects are placed within the basin; and remote control of a thermal treatment system (e.g., as disclosed in U.S. Pat. No. 6,371,121).

However, when insignificant amounts of liquid are present within a thermal treatment system basin, the system heating and cooling mechanisms operate with minimal thermal resistance, thereby enabling the mechanisms to become damaged. Further, the drapes employed by the system may be damaged by being disposed proximate the heating or cooling mechanism without having the liquid to absorb the thermal energy. Since only sterile drapes are to be used during surgical procedures, a leak in a surgical drape compromises sterility and contaminates the entire surgical procedure, thereby increasing the risk of injury to a patient.

The related art has attempted to overcome this problem by employing sensing devices with surgical drapes. For example, U.S. Pat. No. 5,524,643 (Faries, Jr. et al.) discloses a surgical drape combined with a sensor, preferably attached to the drape, to detect the presence of liquid within a drape container conforming to a heating/cooling thermal treatment system basin. An alternative embodiment employs sensors at opposite surfaces of the drape to measure conductance and, thereby, leakage through the drape. A microprocessor of each embodiment receives a signal representing, for example, an electrical conductance measurement and determines the presence of liquid and/or a leak. If liquid is not present or a leak is determined to exist, the microprocessor disables a temperature controller for the basin to prevent damage to the drape and heating and cooling mechanisms.

U.S. Pat. No. 5,816,252 (Faries, Jr. et al.) discloses a drape for use with a system for thermally treating a sterile medium. The drape includes liquid sensitive material that changes color upon contact with liquid to indicate the presence of a leak. The liquid sensitive material may be placed between the drape and a receiving basin or affixed to the drape in the form of indicia symbolically directing placement of the drape over the system. The system may include a single basin and be of the type that either thermally cools or heats the sterile medium, or the system may include a plurality of basins with each basin either thermally cooling or heating the sterile medium. The liquid sensitive material detects leaks within the drape while assisting the operator in properly aligning and placing the drape over the system.

U.S. Pat. No. 6,102,044 (Naidyhorski) discloses an electrode carrying surgical drape including a polymeric film having opposing surfaces and an electrode receiving aperture therethrough. An electrode is disposed through the aperture, while patches sealingly affix electrode portions to each of the opposing surfaces of the polymeric film in the vicinity of the aperture to form a reinforced laminated structure capable of maintaining the sterility of an established sterile field.

The above-described systems can stand some improvement. In particular, the Faries, Jr. et al. sensor drape (U.S. Pat. No. 5,524,643) employs a plug connector disposed through the drape to facilitate connections between the drape sensor and the thermal treatment system, thereby complicating the process of effectively sealing the drape to prevent contamination of the sterile field. Further, the drape is required to be placed on the system with the plug aligned with a corresponding plug receptacle for system operation, thereby restricting the manners in which the drape may be positioned on the system to form the drape container. The Faries, Jr. et al. system employing liquid sensitive material with a drape (U.S. Pat. No. 5,816,252) indicates the presence of a leak within the drape container. However, this system relies on operating room personnel to respond to the leak indication and perform appropriate actions with respect to system operation. Thus, the system may continually operate in the presence of a drape container leak until personnel notice and respond to the leak indication, thereby increasing the risk of contamination of a surgical procedure and damage to the system heating or cooling mechanism when a drape leak occurs. Since the Naidyhorski drape includes an electrode disposed therethrough, the drape utilizes additional materials (i.e., a plurality of patches) to seal the electrode through the drape, thereby increasing system materials, complexity and costs.

OBJECTS AND SUMMARY OF THE INVENTION

Accordingly, it is an object of the present invention to detect the presence of solution and/or a leak within a drape container disposed in a thermal treatment system basin and control system operation in accordance with detected drape container conditions.

It is another object of the present invention to employ a sterile surgical drape constructed of conductive and insulating drape portions to detect conditions within a drape container formed in a thermal treatment system basin.

Yet another object of the present invention is to employ a surgical drape constructed of conductive and insulating drape portions to serve as solution and/or leak sensors with a thermal treatment system including circuitry that interfaces the drape to control system operation in accordance with drape container conditions detected by the drape conductive portions and circuitry.

The aforesaid objects may be achieved individually and/or in combination, and it is not intended that the present invention be construed as requiring two or more of the objects to be combined unless expressly required by the claims attached hereto.

According to the present invention, a drape constructed of conductive and insulating drape portions or segments is disposed over a top surface of a thermal treatment system having a basin recessed therein. A portion of the drape is pushed down into, and conforms to, the basin to form a drape container or receptacle within the basin for collecting a sterile medium. The thermal treatment system may be of the type that either heats or congeals the sterile medium to respectively produce a warm sterile liquid or sterile slush within the basin. The conductive segments provide a signal indicating the presence of liquid and/or leaks within the drape container to the system to facilitate control of system operation. In addition, a drape utilized for a plural basin thermal treatment system may include the conductive and insulating drape segments for each basin. The plural basin drape forms a drape receptacle within each basin that may either heat or congeal the sterile medium as described above. The conductive and insulating drape segments are typically disposed within each drape receptacle to detect the presence of liquid and/or a leak within that drape receptacle. The conductive segments further provide a signal to the system to facilitate control of system operation in substantially the same manner described above.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

Figure 1:
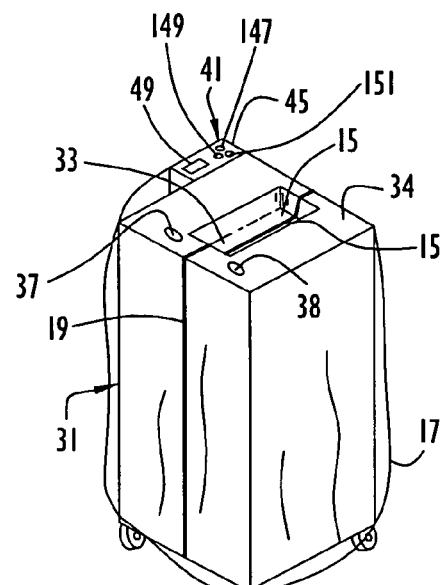
FIG. 1 is a view in perspective of a surgical drape placed over an exemplary thermal treatment system to detect fluid and leaks within a thermal treatment system basin according to the present invention.

An exemplary thermal treatment system and drape to heat a sterile medium (e.g., solution or liquid) and detect drape container conditions according to the present invention is illustrated in FIG. 1. Specifically, the system includes a cabinet or housing 31, a wiring housing 45 attached to the cabinet and a warming basin 33 recessed into a cabinet top surface 34. Basin 33 may be of any shape, however, by way of example only, the basin is illustrated as being substantially rectangular. A power switch 37 and a temperature controller/indicator 38 are provided on top surface 34 toward the cabinet front wall with the warming basin residing between the power switch and controller. Wiring housing 45 is attached to the cabinet side wall that is closest to power switch 37 and facilitates connections as described below. A heater 70 (FIG. 4) is disposed on the underside and/or sides of the basin to heat the basin and a sterile medium contained therein. The heater is controlled by controller 38 in accordance with an entered desired temperature and temperatures measured by a temperature sensor 72 (FIG. 4) as described below. Heater 70 is typically implemented by a conventional etched foil silicon rubber heating pad and is attached to the basin via a pressure sensitive or other type of adhesive. The heater may alternatively be of any quantity (e.g., at least one), shape or size, and may include any configuration (e.g., strips, bars, segments, etc.) that covers the entirety or any portion of the basin. In addition, the heater may be implemented by any conventional or other type of heater or heating element (e.g., heating coils, etc.) that may be disposed on the basin at any suitable locations.

Temperature sensor 72 is preferably implemented by a conventional resistive temperature device (RTD) (e.g., a 1,000 Ohm RTD). However, the sensor may be implemented by any conventional or other type of temperature sensor, and may be disposed at any suitable location on the basin or within the cabinet. It is to be understood that the thermal treatment system described above may have various configurations. For example, the thermal treatment system may be configured to cool and/or congeal the medium to produce cooled liquid or surgical slush. In this instance, the heater may be replaced by refrigeration devices that are controlled in substantially the same manner described below in response to detection of solution and leaks within the drape container. Further, the thermal treatment system may include a plurality of basins warming and/or cooling a sterile medium. Examples of warming, cooling and/or plural basin systems are disclosed in several of the above-mentioned Faries, Jr. et al. (e.g., U.S. Pat. Nos. 5,333,326; 5,429,801; 5,522,095; 5,524,643; 5,615,423; 5,653,938; 5,816,252; 5,862,672; 5,857,467; 5,879,621; 6,091,058; and 6,255,627).

A sterile drape 17, preferably transparent, is typically disposed over the top and sides of cabinet 31 and made to conform to the side wall and bottom of basin 33. Power switch 37 and controller 38 are disposed on top surface 34 of system cabinet 31 and are adjustable manually through drape 17. The portion of drape 17 disposed in basin 33 serves as a sterile container or receptacle for sterile liquid placed therein to be heated. Typical sterile liquid treated by the thermal treatment system is a 0.80% to 0.95% sodium chloride solution (i.e., saline). Drape 17 is made from materials that are impervious to the sterile liquid and sufficiently soft and flexible to conform to a basin wall as described below. The thickness of the drape is preferably minimized to render thermal transfer therethrough most efficient, yet the thickness is sufficient to resist tearing and puncturing during normal use. The drape is designed to be disposable after a single use and is provided pre-sterilized and prepackaged in a manner to preserve its sterile state during storage.

The drape is typically positioned over the thermal treatment system with a portion of the drape disposed in a basin to form a drape receptacle as described above. The drape forms a sterile field above the basin to maintain sterility of the sterile medium. However, a puncture, tear or other opening in the drape disrupts the sterile field and may contaminate the sterile liquid, thereby risking injury to a patient. Further, the thermal treatment system may damage the drape (e.g., via the heating or refrigeration device) in the event that liquid is not present within the drape container.

Figure 2:
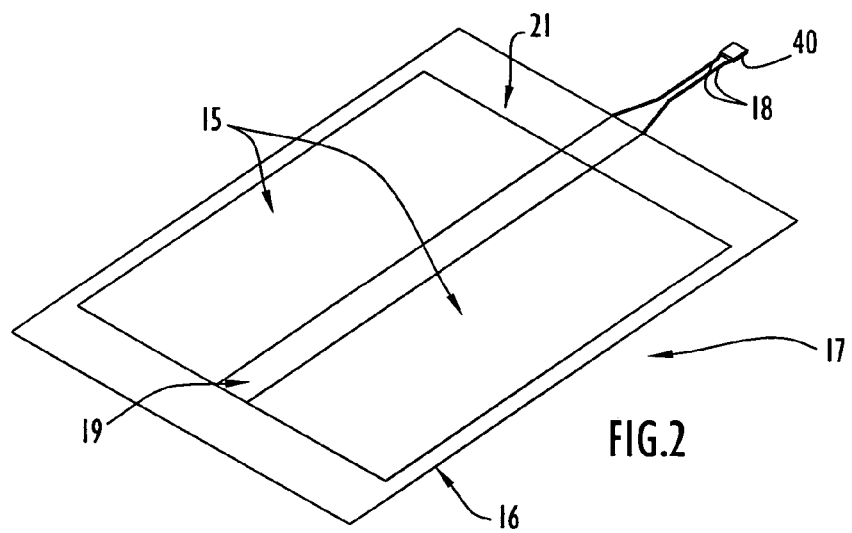
FIG. 2 is a view in perspective of an exemplary surgical drape of the present invention for detecting the presence of fluid and leaks within a thermal treatment system basin.
Figure 3:
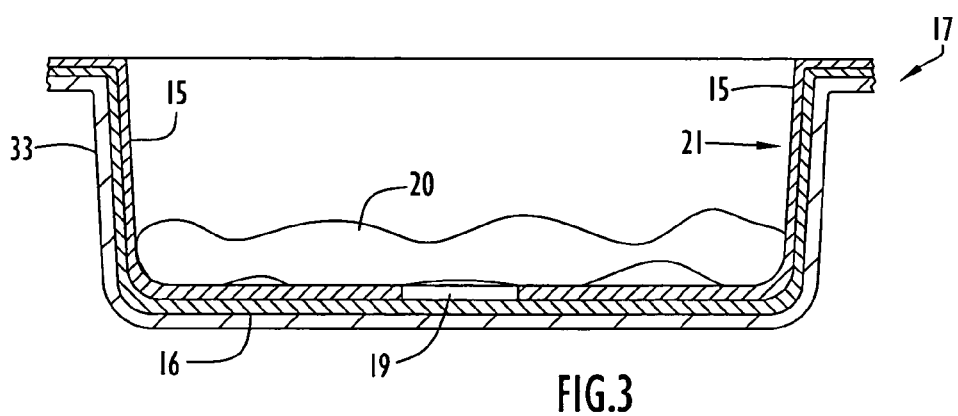
FIG. 3 is a side view in elevation and partial section of the surgical drape of FIG. 2 containing fluid within a thermal treatment system basin.

In order to detect the presence of liquid and/or leaks within the drape container to maintain drape integrity and sterility of the sterile medium, drape 17 is constructed of or includes a combination of conductive and insulating materials as illustrated, by way of example only, in FIGS. 2-3. Specifically, drape 17 includes a detection layer 21 and an insulating layer 16. The drape is substantially rectangular or square, but may be of any shape or size to accommodate the basin and thermal treatment system. The detection layer is attached to a top surface of the insulating layer and basically forms a sterile drape surface for contacting sterile liquid 20. The layers may be attached via any conventional or other techniques (e.g., formed integral, heat welded, etc.). The detection layer may be of any shape or size, and includes a plurality of conductive segments 15 and at least one insulating segment 19. The drape is primarily constructed of polymeric materials and may also be made of polyurethane film as disclosed for the drape in U.S. Pat. No. 4,934,152 (Templeton). The conductive segments are preferably constructed of polymeric materials with electrical conducting properties, such as conductive polymers (e.g., polypyrrole, etc.), an electrically conductive carbon filled polymer film, an electrically conductive polymer nanocomposite material and a microporous polymer sheet as disclosed in U.S. Pat. No. 6,524,742 (Emanuel et al.), the disclosure of which is incorporated herein by reference in its entirety. The insulating segment is preferably formed of conventional polymeric materials that have minimal or no electrical conducting properties, such as those materials commonly used in hospitals for surgical drapes and polyurethane. The segments are arranged to enable the insulating segment to electrically isolate the conductive segments. In other words, an insulating segment is typically disposed between adjacent conductive segments. The conductive and insulating segments may be of any shape or size and may be arranged in any fashion that electrically isolates the conductive segments from each other.

In addition, the drape may further include a preformed container portion contoured to match the contour of a basin. The detection and/or insulating layers of the preformed container portion may be (but are not necessarily) thicker than the layers of the remaining portions of the drape described above in order to resist puncture and enable the container portion to maintain the shape of the basin. By way of example only, the detection layer of the container portion may be made of the materials described above, while the insulating layer of the container portion may be made of a heavy gauge polyethylene/ionomer resin blend. The percentage of ionomer resin in the blend is typically (but not necessarily) in the approximate range of forty to seventy percent. However, the preformed container portion may be constructed of any suitable conductive and non-conductive materials. The conductive and insulating segment arrangement may cover the preformed container and/or any other portion of the drape in any fashion.

By way of example only, drape 17 includes two conductive segments 15 and an insulating segment 19 disposed edge to edge therebetween. Insulating segment 19 is generally rectangular and disposed along a centerline of the drape. Conductive segments 15 are each substantially rectangular and disposed adjacent respective opposing longer dimensioned sides of insulating segment 19. Segments 15, 19 have substantially the same longer dimensions, while the shorter dimensions of conductive segments 15 are substantially greater than those of insulating segment 19. Basically, insulating segment 19 is in the form of a strip disposed with its opposite edges sealingly abutting respective edges of the conductive segments to electrically isolate those segments. The insulating and conductive segments may be of any shape or size, and may cover any portion of the detection layer (e.g., the entire layer or any portion thereof, the portion of the layer for placement in a basin, etc.).

Insulating layer 16 forms the non-sterile drape surface and contacts the thermal treatment system and basin. The insulating layer may be of any shape or size, but preferably includes dimensions sufficient to be placed over the thermal treatment system top surface (and within the basin) and hang down therefrom along the cabinet side walls. The insulating layer isolates the detection layer from the basin and thermal treatment system to prevent formation of electrical paths between conductive segments via the basin and/or system. The insulating layer further enables detection of leaks within the drape container as described below.

Conductive segments 15 may be viewed as electrodes separated by insulating segment 19. Electrical leads or conductors 18 comprise part of each electrode and are connected to or formed integral with conductive segments 15 to couple the segments to detection circuitry 100 (FIG. 4) within the thermal treatment system. Leads 18 are preferably (but not necessarily) formed of the same material that comprises the conductive segments and may terminate in a plug or other connector 40, and may extend from the detection layer through the drape or traverse a drape peripheral edge to the non-sterile drape side. The leads may further include or be encompassed within insulating material to electrically isolate the leads from the thermal treatment system and/or basin.

The potential of and across the conductive segments is measured by the detection circuitry within the thermal treatment system to determine the presence of fluids and/or leaks within the drape container. In particular, the detection circuitry initially applies a reference voltage or potential to leads 18 (e.g., and thereby to conductive segments 15). Since current flow between conductive segments 15 is prevented by insulating segment 19 and insulating layer 16 as described above, the potential of and between leads 18 basically remains unchanged.

When the sterile medium is placed in the drape container, the sterile medium contacts the conductive segments, thereby forming an electrical path or conductive bridge between the electrodes comprising those segments. Accordingly, current flow between the conductive segments is initiated in response to the conductive segments contacting liquid, thereby causing a change in the potential of and between leads 18. Further, the presence of a leak within the drape container enables current to flow between the conductive segments and ground (e.g., the basin beneath the drape), thereby causing a further change in the potential of and between leads 18. The current flow (or lack thereof) resulting from each of the above conditions is detected by the detection circuitry within the thermal treatment system. This is typically accomplished by detecting the potential or voltage of and between leads 18. The magnitude of the voltage or voltage change is utilized by the detection circuitry to detect the presence of the drape and/or the presence of solution and/or leaks within the drape container and to control system operation in accordance with the detected conditions as described below. For example, the detection circuitry may disable the thermal treatment system in response to the absence of liquid and/or drape or the presence of a leak within the drape container.

Wiring housing 45 (FIG. 1) receives signals from conductive segment electrodes 18 and includes wiring to transfer signals between that housing and detection circuitry 100 (FIG. 4) to facilitate detection of liquid and/or leaks within the drape container. Wiring housing 45 is in the form of a generally rectangular box and is mounted on a cabinet side wall toward the cabinet rear portion. The wiring housing includes a receptacle 49 for receiving connector 40 and indicators 41, preferably in the form of light emitting diodes 147, 149 and 151 to indicate drape container conditions. By way of example only, the wiring housing includes: green diode 147 to indicate operation of the system (e.g., solution present without a drape container leak); yellow diode 149 to indicate the absence of solution and leaks within the drape container; and red diode 151 to indicate the presence of a leak within the drape container.

Electrical leads 18 may extend from conductive segments 15 and through the drape to the non-sterile drape side for engagement with the wiring housing, thereby connecting the drape to detection circuitry disposed within the cabinet as described below. Alternatively, the leads may extend from the detection layer and traverse a drape peripheral edge to the non-sterile drape surface for engagement with the wiring housing. The wiring housing and/or receptacle may alternatively be disposed at any location on cabinet 31 (e.g., top surface, side walls, cabinet interior, etc.).

The detection circuitry basically prevents system operation (e.g., disables controller 38) in response to a leak or the absence of liquid within the drape container, or in response to the absence of a connection between the drape and the thermal treatment system. In other words, the detection circuitry determines the drape container or other conditions based on the electrode signals and controls system operation accordingly. In addition, the detection circuitry may selectively illuminate the diodes to indicate the particular determined drape container conditions (e.g., no fluid, the presence of a leak, etc.). The wiring housing receives connector 40 within receptacle 49 and facilitates connections via appropriate wiring between the receptacle, diodes and a circuit board 52 (FIG. 4) of the detection circuitry containing a condition circuit 53 (FIG. 5) as described below. Fuses may be employed to protect the system circuitry from power surges and/or spikes that may cause damage to the system. The wiring connections between the receptacle, diodes, fuses and/or circuit board may be substantially similar to those described in the aforementioned patent applications.

Figure 4:
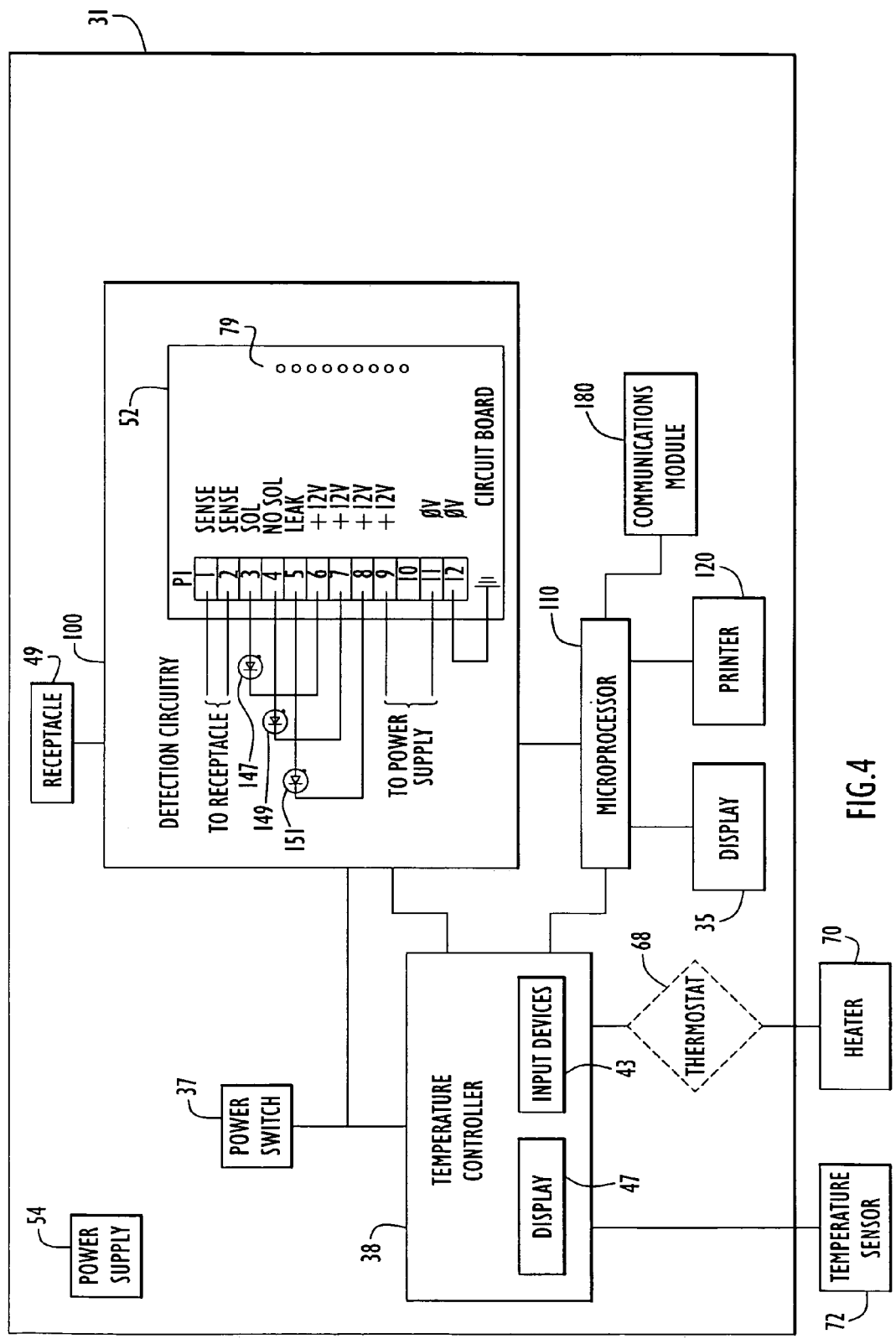
FIG. 4 is block diagram of control circuitry for the system of FIG. 1.

Referring to FIGS. 1 and 4, cabinet 31 houses control circuitry including power switch 37, temperature controller 38, receptacle 49, a power supply 54 and detection circuitry 100. Power supply 54 provides appropriate power signals to the control circuitry components and includes a receptacle to receive signals from a power cord interfacing a conventional wall outlet jack. The power switch enables power to the circuitry components and may be implemented by any conventional or other switching device. Plug or connector 40 is received in receptacle 49 to provide signals from leads 18 (or the electrodes) to the detection circuitry. This further enables the detection circuitry to detect the presence of a drape on the system as described above. The temperature controller controls the heater, while the detection circuitry determines the drape container conditions based on the electrode signals and controls the temperature controller accordingly. The wiring housing may include audio and/or visual indicators 41 (e.g., beeper or buzzer, speaker 197 (FIG. 5), various colored light emitting diodes (e.g., green diode 147, yellow diode 149 and red diode 151), etc.) to indicate drape container conditions as described above. The detection circuitry may selectively actuate the indicators in any fashion to indicate the particular determined drape container conditions (e.g., absence of the drape or solution, the presence of a leak, etc.). The control circuitry components may be disposed on and/or within the cabinet and/or wiring housing in any fashion at any desired locations.

Temperature controller 38 is connected to heater 70 and temperature sensor 72 to control the heater in response to a desired or set point temperature entered by a user and the temperature measured by the temperature sensor. In particular, temperature controller 38 is typically implemented by a conventional temperature controller or microprocessor and includes a display 47 and input devices 43 (e.g., buttons, keys, etc.). The temperature controller controls power to the heater based on a comparison of the temperature measured by temperature sensor 72 and the set point temperature entered by the user via input devices 43. The temperature controller may further display the measured and/or set point temperatures or any other desired information on display 47. The information to display may be selected by a user via input devices 43. When the measured temperature exceeds the set point temperature, controller 38 disables or reduces power to the heater. Conversely, when the measured temperature is below the set point temperature, controller 38 enables or increases power to the heater. A thermostat 68 may be disposed between the controller and heater to disable current to heater 70 in response to a temperature measurement exceeding a temperature threshold. The thermostat disables the heater in response to detection of excessive heater temperatures and may be implemented by any conventional switching type or limiting devices, such as a high limit thermostat, and disposed at any suitable location.

Temperature controller 38 further controls heater 70 in response to signals received from detection circuitry 100. The detection circuitry detects the presence of solution and leaks within the drape container and provides appropriate signals to temperature controller 38. The detection circuitry basically disables the temperature controller (and heater) in response to absence of the drape, absence of solution within the drape container and/or the presence of a drape container leak as indicated by the electrode signals. The detection circuitry may be substantially similar to the detection circuitry disclosed in the aforementioned patent applications. Alternatively, the detection circuitry may include a microprocessor to process electrode signals and control the indicators, heater or any other devices. In this case, electrode signals are converted to digital signals and compared by the microprocessor to threshold levels for each condition. The microprocessor may generate the appropriate control signals to control basin thermal devices and various indicators in accordance with the determined conditions. The microprocessor may be implemented by or implement the temperature controller and/or processor 110 described below.

Exemplary detection circuitry for the system includes circuit board 52 including condition circuit 53 and green, yellow and red diodes 147, 149, 151 indicating the drape container conditions. The circuit board further includes a series of pins or terminals 1-12 to facilitate connections and a plurality of indicator lights 79. By way of example only, pins 1 and 2 are connected to wiring housing receptacle or connector 49 to receive electrode signals, while pins 9 and 11 are connected to the positive and reference terminals of power supply 54, respectively. Pins 6-8 are connected to pin 9 and provide a voltage (e.g., +12V DC) to the condition circuit, while pin 12 is connected to pin 11 and provides a ground. Green diode 147 is connected between pins 3 and 6 and is illuminated in response to detection of solution within the drape container without a leak, while yellow diode 149 is connected between pins 4 and 7 and is illuminated in response to detection of the absence of solution and a leak within the drape container. Red diode 151 is connected between pins 5 and 8 and is illuminated in response to detection of a leak within the drape container. Pin 10 is basically inoperable and utilized to facilitate compatible connections with the board.

Figure 5:
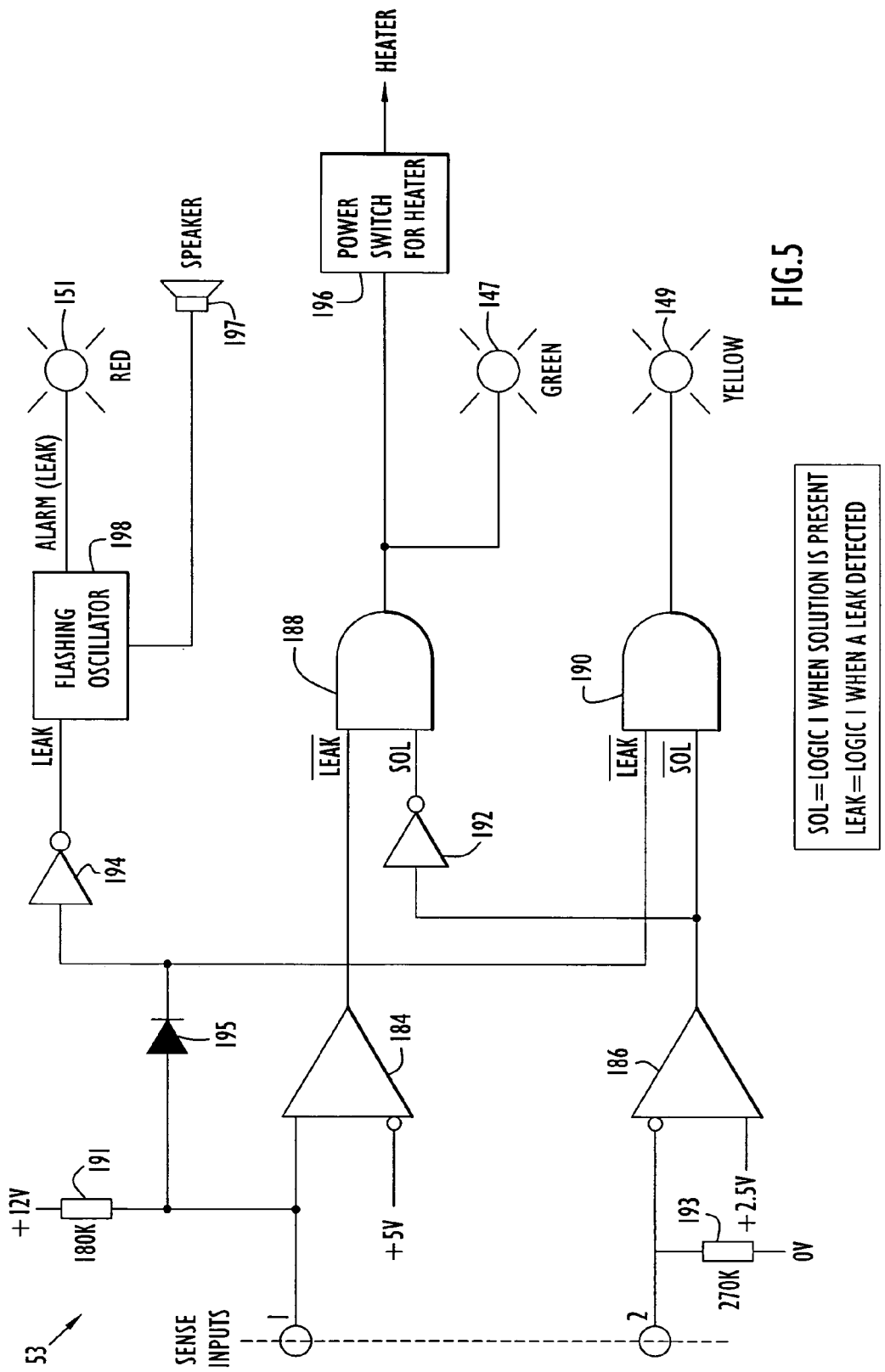
FIG. 5 is a schematic block diagram of an exemplary condition circuit of the detection circuitry within the control circuitry of FIG. 4 for determining the presence of liquid and/or leaks within a drape container.
Figure 6A:
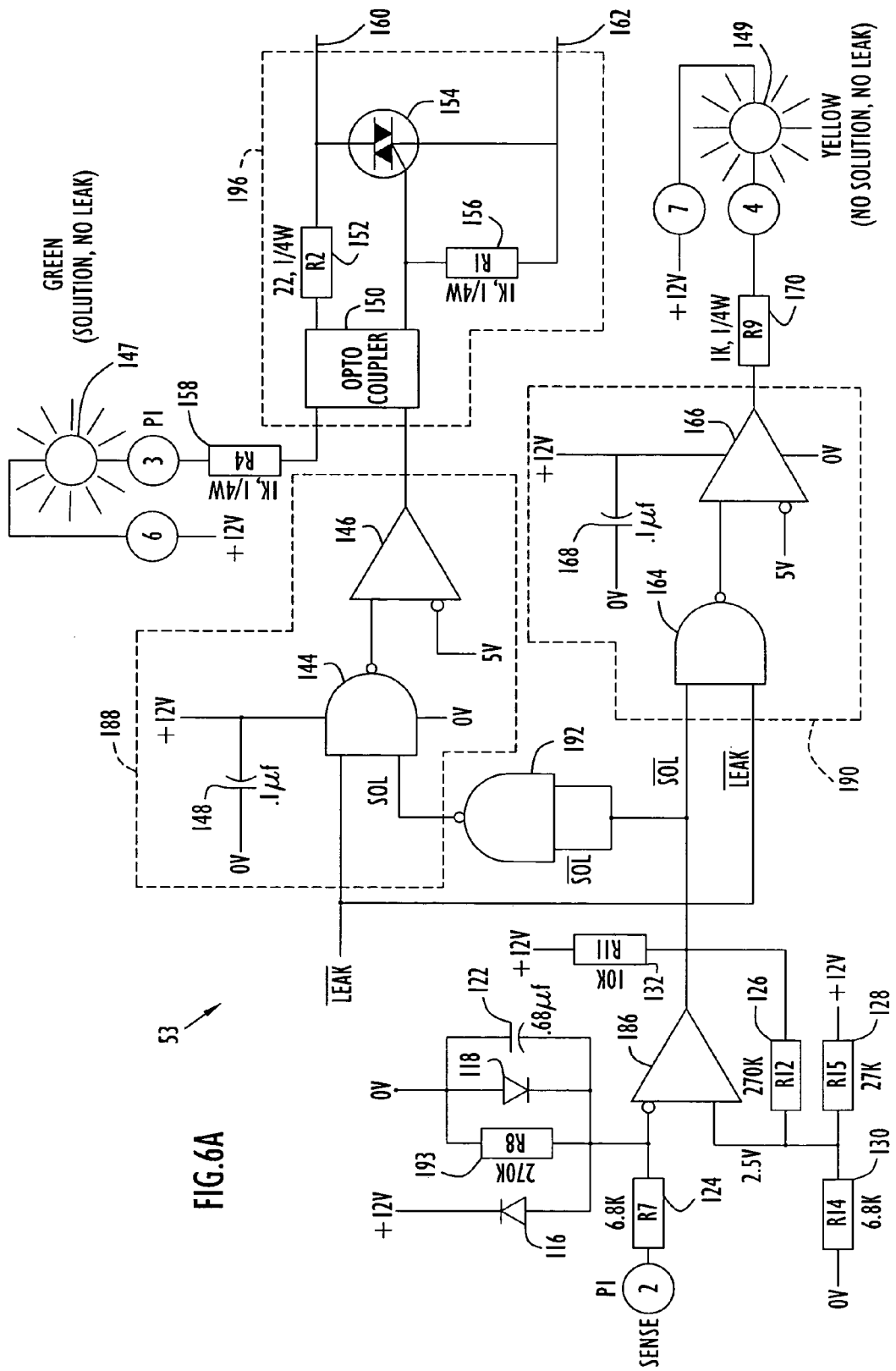
FIGS. 6A-6B are detailed electrical schematic diagrams of the exemplary condition circuit of FIG. 5.
Figure 6B:
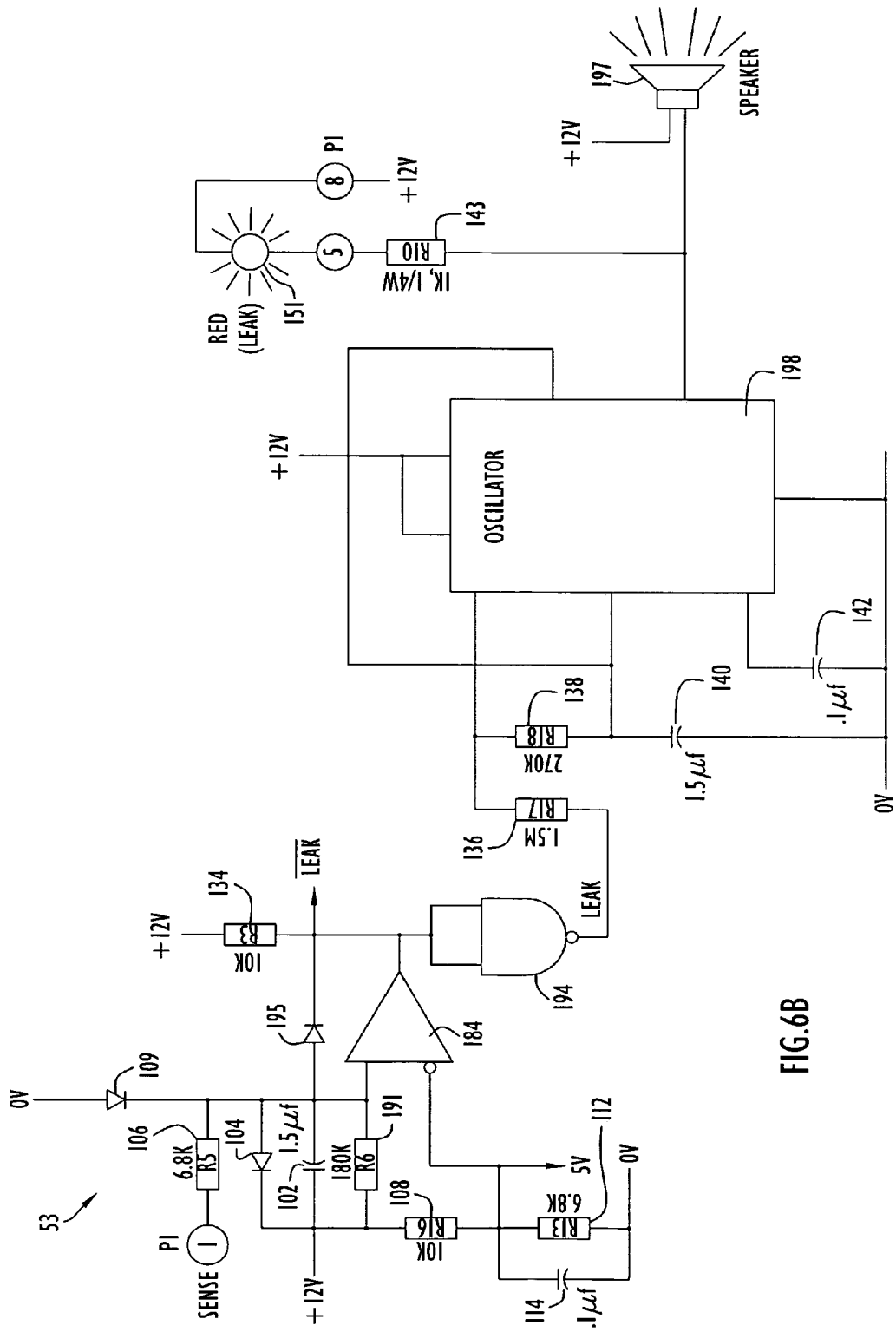

An exemplary condition circuit 53 for detecting the presence of solution and leaks within the drape container is illustrated in FIGS. 5, 6A and 6B. Initially, the condition circuit prevents operation of the thermal treatment system in the event a drape is damaged (e.g., contains a leak) or not connected to the detection circuitry, or in the event solution is absent from the drape container. The condition circuit is coupled to leads 18 (or the electrodes) via pins 1 and 2 of circuit board 52. The presence of solution within the drape container causes current flow between the conductive segments (and leads), while a leak facilitates current flow between the conductive segments (and leads) and ground as described above. Accordingly, the current flow causes a voltage change at pins 1 and 2 of the circuit board, thereby enabling detection of solution and leaks by the condition circuit. In particular, the condition circuit includes comparators 184, 186, logic circuitry 188, 190, inverters 192, 194, a power switch 196 and an oscillator 198. Pin 1 of circuit board 52 is connected to the non-inverting input of comparator 184, while that input is further connected to a resistor 191 (e.g., 180K Ohm) disposed in series with a supply voltage (e.g., 12V DC). The non-inverting input of comparator 184 is further coupled to additional circuitry (FIG. 6B) (e.g., a resistor 106 (e.g., 6.8K Ohm) connected in series with pin 1, a resistor 108 (e.g., 10K Ohm) coupled to resistor 191 and the supply voltage, a diode 104 connected in parallel with resistor 191, a capacitor 102 (e.g., 1.5 µf) connected in parallel with resistor 191 and diode 104, and a diode 109 connected between the input and a ground potential) to protect the circuit from damage in the event an external voltage is applied to pins 1 and 2 and to provide filtering to prevent a response to noise. A diode 195 is disposed in a feedback path of comparator 184 to maintain the state of a particular condition as described below. The inverting input of comparator 184 is similarly coupled to additional circuitry (FIG. 6B) (e.g., a resistor 112 (e.g., 6.8K Ohm) connected between resistor 108 and a ground potential, and a capacitor 114 (e.g., 0.1 µf) connected in parallel with resistor 112) to enhance circuit performance. Resistors 108 and 112 basically provide the comparator inverting input with a reference voltage (e.g., 5V DC). Comparator 184 determines the presence of a drape container leak by comparing the input of pin 1 to the reference voltage (e.g., 5V DC). If pin 1 exceeds the reference voltage, the comparator provides a high level logic signal indicating the absence of a leak (e.g., the signal $\overline{\text{LEAK}}$ in the figures indicates the absence of a drape container leak when attaining a high logic level); otherwise a low level logic signal indicating the presence of a leak is produced by the comparator.

Pin 2 is connected to the inverting input of comparator 186, while that input is further connected to a resistor 193 (e.g., 270K Ohm) disposed between the comparator input and a ground potential. The inverting input is further coupled to additional circuitry (FIG. 6A) (e.g., a resistor 124 (e.g., 6.8K Ohm) connected in series with pin 2, a diode 116 connected in series with a supply voltage (e.g., 12V DC), a diode 118 connected in parallel with resistor 193, and a capacitor 122 (e.g., 0.68 µf) connected in parallel with resistor 193 and diode 118) to protect the circuit from damage in the event an external voltage is applied to pins 1 and 2 and to provide filtering to prevent a response to noise. The non-inverting input of comparator 186 is coupled to additional circuitry (FIG. 6A) (e.g., a resistor 126 (e.g., 270K Ohm) connected in a comparator feedback path, a resistor 128 (e.g., 27K Ohm) connected between the non-inverting input and a supply voltage (e.g., 12V DC), a resistor 130 (e.g., 6.8K Ohm) connected between the non-inverting input and a ground potential, and a resistor 132 (e.g., 10K Ohm) connected between a supply voltage (e.g., 12V DC) and the comparator output) that basically provides a reference voltage (e.g., 2.5V DC) for the comparator non-inverting input. Comparator 186 determines the presence of solution within the drape container by comparing the input of pin 2 with the reference voltage. If the reference voltage (e.g., 2.5V) exceeds pin 2, the comparator produces a high level logic signal indicating the absence of solution within the drape container (e.g., the signal $\overline{\text{SOL}}$ in the figures indicates the absence of solution within the drape container when attaining a high logic level); otherwise a low level logic signal indicating the presence of solution is produced.

The output of comparator 184 is coupled to inverter 194, to an input of logic circuitry 188 and to an input of logic circuitry 190. The comparator output is further coupled to additional circuitry (FIG. 6B) (e.g., a resistor 134 (e.g., 10K Ohm) connected between the comparator output and a supply voltage (e.g., 12V DC)) to enhance circuit performance. Inverter 194 is in the form of a NAND gate (FIG. 6B) and inverts the comparator output. Since comparator 184 provides a low level logic signal in response to the presence of a leak as described above, inverter 194 inverts the comparator output to provide a high level logic signal in response to a leak (e.g., the signal LEAK in the figures indicates the presence of a drape container leak when attaining a high logic level). The inverter is connected to a timer 198 that serves as a low frequency oscillator and is actuated by the high level logic signal produced by inverter 194 in response to the presence of a leak. Additional circuitry (FIG. 6B) (e.g., a resistor 136 (e.g., 1.5M Ohm) connected in series with the NAND gate output, a resistor 138 (e.g., 270K Ohm) connected between timer inputs, a capacitor 140 (e.g., 1.5 µf) connected between resistor 138 and a ground potential, and a capacitor 142 (e.g., 0.1 µf) connected between a timer input and the ground potential) is connected to and/or between the inverter and oscillator to enhance actuation of the oscillator in response to a high level logic signal from the inverter. The oscillator output is coupled to a reference terminal of a speaker 197 and to pin 5 for actuating red diode 151. A resistor 143 (e.g., 1K Ohm) is disposed between pin 5 and the oscillator output, while a speaker positive terminal is connected to a supply voltage (e.g., 12V DC). The oscillator output is in the form of a pulse train that provides periodic low level logic signals. The low level signals provide a sufficient voltage differential to enable the supply voltages of the red diode (e.g., 12V DC of pin 8) and speaker (e.g., 12V DC of the speaker positive terminal) to drive those devices. Thus, the oscillator produces a pulse train that enables the diode to flash and the speaker to beep at rates proportional to the pulse train frequency when a leak is present in the drape container.

Conversely, when a leak is absent from the drape container, comparator 184 provides a high level logic signal as described above. Inverter 194 inverts the comparator output to provide a low level logic signal in response to the absence of a leak. The low level logic signal is insufficient to actuate oscillator 198, thereby disabling red diode 151 and speaker 197 when a leak is not present within the drape container.

Logic circuitry 188 determines the presence of conditions to enable the heater (e.g., solution is present within the drape container without a leak). The logic circuitry is coupled to outputs of comparators 184 and 186. An inverter 192 in the form of a NAND gate (FIG. 6A) is disposed between logic circuitry 188 and comparator 186 to invert the comparator output. Since comparator 186 produces a low level logic signal in response to the presence of solution within the drape container as described above, inverter 192 inverts the comparator output to provide a high level logic signal in response to the presence of solution (e.g., the signal SOL within the figures indicates the presence of solution within the drape container when attaining a high logic level). Logic circuitry 188 combines the signals (e.g., $\overline{\text{LEAK}}$, SOL) from comparator 184 and inverter 192, indicating leak and solution conditions, and provides a signal to illuminate green diode 147 and actuate power switch circuitry 196 to enable heater 70 in response to the signals indicating the presence of solution without a leak in the drape container.

Logic circuitry 188 (FIG. 6A) includes a NAND gate 144 and a comparator 146. The NAND gate receives output signals from comparator 184 and inverter 192 and produces a low level logic signal in response to the signals indicating the presence of solution in the drape container without a leak. The NAND gate output is connected to the non-inverting input of comparator 146, while the comparator inverting input is connected to a reference voltage (e.g., 5V DC). The comparator produces a low level logic signal in response to a low NAND gate output in order to drive power switch circuitry 196 to enable heater 70 when solution is present within the drape container without a leak. NAND gate 144 is further coupled to additional circuitry (e.g., a ground potential coupled to a gate terminal, a supply voltage (e.g., 12V DC) coupled to another gate terminal with a capacitor 148 (e.g., 0.1 µf) connected between that gate terminal and a ground potential) to enhance gate operation.

Power switch circuitry 196 includes an optocoupler 150 and a triac 154. The triac is connected between conductors 160, 162 that provide signals to temperature controller 38, and has a gate terminal coupled to an output of the optocoupler. An optocoupler input is coupled to circuit board pin 3 and, hence, to green diode 147 disposed between circuit board pins 3 and 6, while a resistor 158 (e.g., 1K Ohm) is connected between pin 3 and the optocoupler. The output of comparator 146 indicating drape container conditions is connected to another input of the optocoupler to drive the power switch circuitry in response to the presence of solution without a leak in the drape container as described above. A resistor 152 (e.g., 22 Ohms) is connected to an optocoupler output and in series with the triac, while a resistor 156 (e.g., 1 K Ohm) is connected between the triac gate terminal and conductor 162. A low level logic signal produced by comparator 146 provides a ground that enables the optocoupler input to receive appropriate current to produce outputs that drive the triac. Thus, the low level logic signal from comparator 146 enables actuation of the green diode and triac to indicate the presence of solution without a leak in the drape container and to enable the heater, respectively. The triac provides signals to temperature controller 38 to control actuation of the heater as described above.

Conversely, when a leak is present within, or solution is absent from, the drape container, comparators 184, 186 provide signals that enable NAND gate 144 to produce a high level logic signal. Comparator 146 generates a high level logic signal in response to the high level NAND gate output, thereby preventing actuation of power switch 196, green diode 147 and heater 70 when a leak is present within, or solution is absent from, the drape container.

Logic circuitry 190 determines the presence of conditions to illuminate yellow diode 149 (e.g., neither solution nor a leak is present within the drape container). The logic circuitry is coupled to the outputs of comparators 184 and 186. Logic circuitry 190 combines the signals (e.g., $\overline{\text{LEAK}}$, SOL) from comparators 184, 186 indicating drape container conditions and provides a signal to actuate yellow diode 149 in response to the comparator signals indicating the absence of solution and a leak within the drape container.

Logic circuitry 190 (FIG. 6A) includes a NAND gate 164 and a comparator 166. The NAND gate receives output signals from comparators 184 and 186 and produces a low level logic signal in response to the comparator signals indicating the absence of solution and a leak within the drape container. The NAND gate output is connected to the non-inverting input of comparator 166, while the comparator inverting input is connected to a reference voltage (e.g., 5V DC). The comparator provides a low level logic signal in response to a low NAND gate output in order to illuminate yellow diode 149. The yellow diode is disposed between circuit board pins 4 and 7 with a resistor 170 (e.g., 1K Ohm) connected between pin 4 and the comparator output. A low level logic signal produced by comparator 166 provides a sufficient voltage differential to enable pin 7 connected to a supply voltage (e.g., 12V DC) to illuminate yellow diode 149. Conversely, when a leak or solution is present within the drape container, comparators 184, 186 provide signals that enable NAND gate 164 to produce a high level logic signal. Comparator 166 generates a high level logic signal in response to the high level NAND gate output, thereby preventing illumination of yellow diode 149 when a leak or solution is present within the drape container.

The condition circuit basically controls system operation in response to detected drape container conditions. The circuit is arranged to enable signals from comparators 184, 186 to selectively facilitate a particular action (e.g., illuminate the red diode and speaker, enable the green diode and heater, or illuminate the yellow diode) in response to the occurrence of corresponding conditions for that action. In other words, a particular action is initiated by the condition circuit in response to the occurrence of corresponding conditions, while remaining actions are disabled. Thus, the green diode and heater are enabled by the condition circuit in response to the presence of solution without a leak in the drape container, and are disabled during occurrence of other drape container conditions (e.g., a leak or no solution within the drape container). Enablement and disablement of the yellow diode and red diode and speaker are facilitated in a similar manner with respect to their corresponding conditions. The condition circuit and/or circuit board may further include circuitry to record the time and/or date when the system or heater is enabled and disabled or any other information. The stored information may be retrieved for hospital records or to assist in evaluating system performance.

The manner in which the condition circuit operates is described, by way of example only, with reference to FIGS. 4-5. Initially, when solution is absent from the drape container, no current flow exists between conductive segments 15 (or between leads 18 (FIG. 2) or the electrodes) and the voltage applied to pins 1 and 2 of circuit board 52 is maintained at a supplied voltage (e.g., twelve and zero volts, respectively). These conditions are similarly present when the drape is disconnected from or incompatible with the system. The output of comparators 184 and 186 are high (e.g., indicating no leak and no solution), thereby enabling logic circuitry 190 to illuminate yellow diode 149 as described above, while the heater, speaker and green and red diodes are disabled as described above.

In the event that solution is present without a leak in the drape container, a conductive path is formed between the conductive segments (and leads 18) and, hence, between pins 1 and 2 of the circuit board. Since the conductive path has a low resistance relative to resistors 191 and 193, these resistors basically form a voltage divider with resistor 191 connected to the supply voltage (e.g., 12V DC) and resistor 193 connected to ground. The voltage divider provides each pin 1 and 2 with an intermediate voltage (e.g., approximately 7.2 V DC). Accordingly, the output of comparator 184 is high (e.g., indicating no leak), while the output of comparator 186 is low (e.g., indicating the presence of solution), thereby enabling logic circuitry 188 to illuminate the green diode and actuate the power switch to enable the heater, while the speaker and red and yellow diodes are disabled as described above.

A leak within the drape container forms a conductive path between the conductive segments (e.g., and, hence, leads 18 and pins 1 and 2) and ground. Thus, the potential of pin 1 is reduced below the comparator reference potential (e.g., 5V DC), thereby causing comparator 184 to produce a low level logic signal. Diode 195 provides feedback to maintain the state of the leak condition until power is disabled. The low output of comparator 184 is inverted by inverter 194, thereby actuating oscillator 198. The oscillator illuminates red diode 151 and actuates speaker 197 to provide an audio leak indication, while the heater and green and yellow diodes are disabled as described above. The output of comparator 186 has no bearing on leak detection and is ignored with respect to actuation of the oscillator. The condition circuit basically generates signals to control the heater and provides visual and audio indications to inform a user of the drape container status.

The condition circuitry may employ any conventional or other components with any desired electrical properties (e.g., resistance, capacitance, etc.) that can perform the above-described functions. The reference voltages utilized by comparators 184, 186 to detect drape container conditions may be any suitable voltages. By way of example only, the reference voltages utilized by those comparators and/or the component electrical properties in the condition circuit may be derived from the properties of the solutions and/or materials of the conductive segments employed. Further, the reference voltages and/or electrical properties may be adjusted to account for objects placed in the basin. For example, placement of conductive objects (e.g., instruments, etc.) within the basin may establish a path for current flow between the conductive segments irrespective of the presence of solution, thereby enabling the condition circuit to indicate erroneous conditions. Accordingly, the reference voltages may be adjusted to differentiate between current flow initiated by solution and the current flow initiated by a conductive object. Alternatively, conductive objects may be utilized in combination with a stand disposed within the basin to elevate the objects above the conductive segments and basin floor in a manner similar to that disclosed in U.S. Pat. No. 6,087,636 (Faries, Jr. et al.).

In addition, the control circuitry may include devices to measure, record and/or provide a report (e.g., hardcopy or electronic form) of system conditions (e.g., time, date, temperature, leak indication, etc.). The report provides medical personnel documentation for their files on the heating characteristics. The primary information produced is the start date and start time of solution heating, the time interval the solution was heated and the temperature the solution attained during heating (e.g., partial or complete history of time and solution temperature). The report may further include a variety of information (e.g., facility name and location, patient information, doctor information, type of procedure, type of solution and/or instruments being heated, amount of solution being heated, etc.). Referring back to FIG. 4, the control circuitry may further include a processor 110, a printer 120 and a communications module 180. These components may be implemented by any conventional or other components performing the functions described herein. Processor 110 is coupled to temperature controller 38 and detection circuitry 100 in order to receive information relating to the basin, liquid temperature, heater temperature and/or drape container conditions. The processor may receive any additional information (e.g., facility information, doctor information, patient information, solution information, instrument information, etc.) from medical personnel or users via processor input devices (not shown).

The processor further maintains the date, elapsed heating time and occurrence time of an event or condition (e.g., the time when a leak occurs, the time when instruments are inserted within the drape container, etc.). The processor may measure the elapsed time or record an occurrence time based on signals received from the temperature controller and/or detection circuitry. For example, the processor may initiate measurement of a time interval in response to the detection circuitry indicating solution within the drape container, and may store the elapsed and/or occurrence time in response to a leak or other condition. The processor may further measure elapsed time or record elapsed and/or occurrence time in response to medical personnel manually entering information on the processor input devices (e.g., start and stop keys). The processor collects the appropriate information and arranges the information into a report. The report may be arranged in any fashion and include any desired information. Moreover, the report and/or information may be stored in a database or memory device (e.g., local memory, removable memory, card, disk, etc.) for later retrieval. In addition, the processor is coupled to a processor or system display 35 to display the elapsed (or running) time, report or any desired information to medical personnel. The information displayed may be selected via the processor input devices, or the display may include display controls (e.g., buttons, keys, etc.). Display 35 may be disposed on the cabinet (FIG. 1) at any desired location.

The processor is further coupled to printer 120 and communications module 180 in order to provide information to a user. The printer basically provides a report in hardcopy form. The processor may control the printer to produce the report at specified times (e.g., termination of heating, at particular times of day, after a particular quantity of uses, etc.) or in response to requests from medical personnel via processor input devices (e.g., print key). The printer may print the report on any desired hardcopy medium. Preferably, the printer places the information onto a label that is attached to a medical file. The information may be printed during or after the solution heating, or be stored on a memory device and printed at a desired time as described above. The printer may further provide additional copies of the report in response to user requests, or a medium automatically creating duplicates may be utilized (e.g., carbon-less paper, etc.). Cabinet 31 may include a slot (not shown) to provide the printed report to a user. However, the slot may be defined at any desired location. Since the cabinet is under the drape adjacent the non-sterile drape side (e.g., the cabinet is non-sterile), the printed report is typically retrieved from the cabinet after completion of the medical procedure (e.g., when the drape is discarded) to preserve sterility.

Communications module 180 enables the report to be provided in electronic form. This module basically facilitates communication with other devices for transference or downloading of the report to those devices. For example, the information may be downloaded or transmitted over a network or other communications medium to another device (e.g., PDA, computer, another thermal treatment system, etc.) for viewing, storage and/or printing. Moreover, the communications module may facilitate retrieval of information (e.g., patient information, facility information, doctor information, solution information, instrument information, etc.) from a database or other source for the report.

Operation of the thermal treatment system with the present invention drape is described with reference to FIGS. 1-4. Initially, drape 17 is placed over the top surface of the thermal treatment system and disposed in basin 33 to form a drape receptacle. Leads 18 of the drape are coupled to wiring housing 45 to connect the drape to the detection circuitry to facilitate detection of drape container conditions. Power switch 37 is actuated and the detection circuitry senses no voltage change across the electrodes (or across the conductive segments or leads), thereby indicating the absence of solution and a leak within the drape container (e.g., the absence of an electrical path between the electrodes). Yellow diode 149 may be illuminated to indicate this condition, while thermal treatment of the basin may be disabled.

A sterile medium is disposed within the drape receptacle and a desired temperature for the medium is entered into the system by the user via controller 38. The sterile medium forms a conductive path between the conductive segments that affects the voltage across the electrodes. The detection circuitry senses the voltage change indicating the presence of solution without a leak in the drape container, and may illuminate green diode 147. Temperature controller 38 subsequently controls thermal treatment of the basin.

When a leak occurs within the drape container, an electrical path is formed between the electrodes and the basin serving as ground, thereby affecting the voltage between the electrodes. The detection circuitry senses the voltage change indicating a leak within the drape container and may disable thermal treatment of the basin. The detection circuitry may further illuminate red diode 151 and/or actuate speaker 197 (FIG. 5) to indicate this condition. Further, processor 110 may receive information from the temperature controller and/or detection circuitry to record the elapsed and/or occurrence time as described above.

Processor 110 may receive appropriate information for a report from the temperature controller, detection circuitry and/or processor input devices at any time (e.g., before, during or after the heating session). The processor arranges the information into a desired report as described above. The report may be produced by printer 120 or transmitted to another device via communications module 180 as described above. The report may be generated in response to termination of a session (e.g., indicated by signals received by processor 110 from the temperature controller and/or detection circuitry) or a request by medical personnel (e.g., via processor or other input devices).

Figure 7:
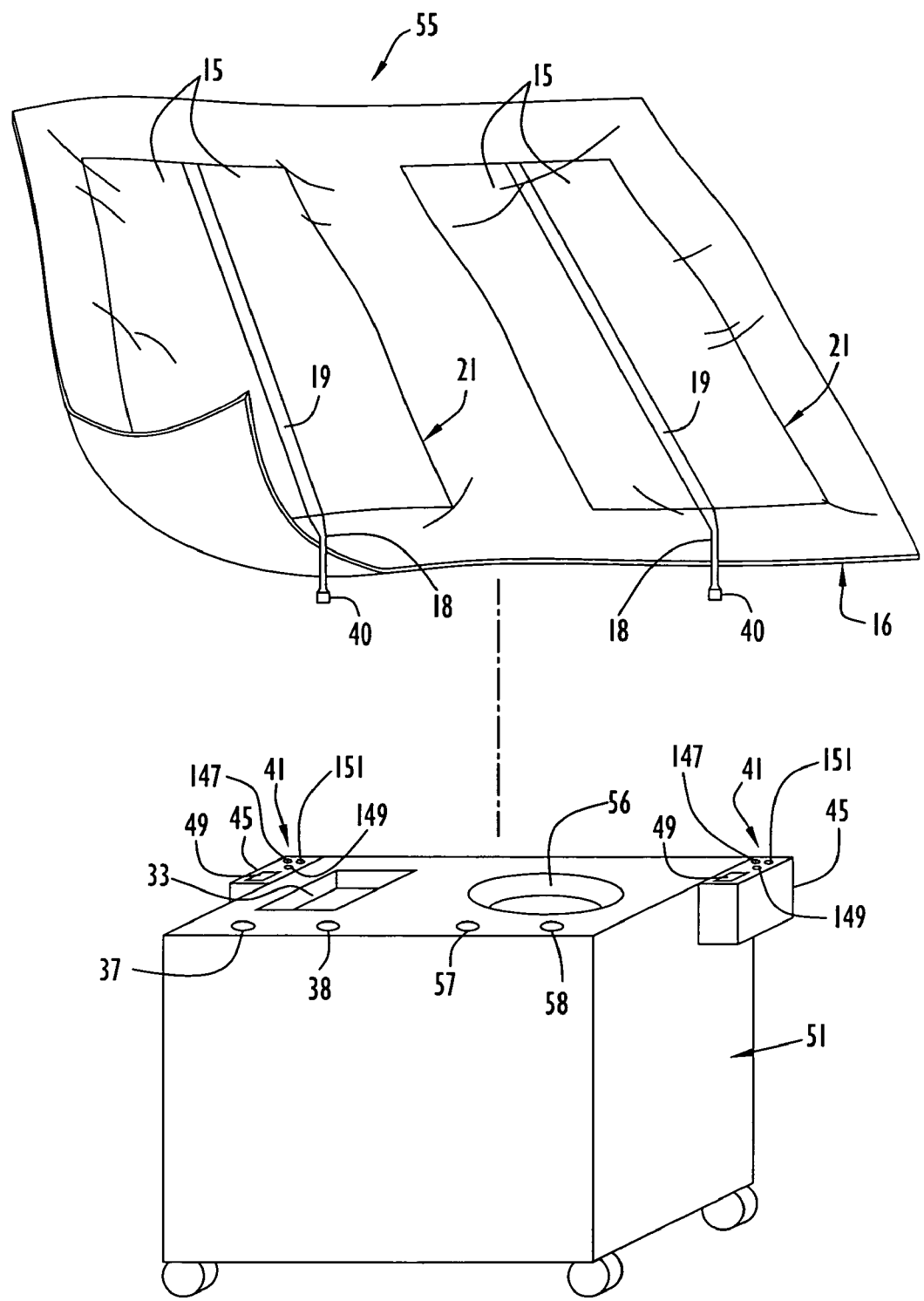
FIG. 7 is an exploded perspective view of a surgical drape including plural conductive and insulating drape segment arrangements for placement over a plural basin thermal treatment system according to the present invention.

It is to be understood that the present invention may be employed for thermal treatment systems including a plurality of basins that either heat or cool the sterile medium. An exemplary plural basin system and corresponding drape according to the present invention are illustrated in FIG. 7. Specifically, the plural basin system includes an integral assembly 51 including warming basin 33 and a substantially circular cooling basin 56 to thermally treat sterile liquid. The system includes power switches 37, 57 and controllers 38, 58 to control operation of the warming and cooling basins, respectively. The assembly further houses the heating and refrigeration devices and control circuitry (not shown) for the individual basins to thermally treat those basins and liquid contained therein as described above.

A drape 55, substantially similar to the drape described above for FIG. 2, is placed over the system and within each basin to form a drape receptacle therein as described above. Conductive and insulating segments 15, 19 and corresponding leads 18 are arranged in the manner described above at appropriate locations on the drape for insertion within a corresponding basin to detect drape container conditions within that basin. Signals from leads 18 or the electrodes are conveyed from each drape container disposed within a basin to a corresponding individual condition circuit associated with that basin to determine drape container conditions and provide signals to control the basin in substantially the same manner described above. The assembly may further include a wiring housing 45 associated with each basin to receive connector 40 of the associated drape container and transfer signals between that housing and a corresponding individual condition circuit in substantially the same manner described above. Each wiring housing typically includes diodes 147, 149, 151 to indicate drape container conditions within a corresponding basin and a receptacle 49 to receive a corresponding connector 40 as described above. The individual basins each basically function in substantially the same manner as the single basin system described above, where the plural basins may be individually controlled or collectively controlled (e.g., all basins enabled or disabled) in response to drape container conditions in a manner similar to that described above.

It will be appreciated that the embodiments described above and illustrated in the drawings represent only a few of the many ways of implementing a surgical drape and method of detecting fluid and leaks in thermal treatment system basins.

The warming, cooling and plural basin systems and their corresponding cabinets, assemblies or housings may be of any shape or size and may be constructed of any suitable materials. The plural basin system may include any quantity of heating and/or cooling basins in any combinations. The basins of the systems may be of any shape or size, may be constructed of any suitable thermal conducting materials (e.g., stainless steel, etc.) and may be disposed at any suitable locations on or within the housings. The systems may include any conventional or other heating and/or refrigeration units to thermally treat the sterile medium or other substance to any desired temperature. The heating unit may include any conventional or other heating device and components to control heating of a basin to any desired temperature (e.g., preferably to temperatures near (e.g., above, at or below) body temperature, such as temperatures in the approximate range of 60° F.-160° F.). The heater may be of any quantity (e.g., at least one), shape or size, and may include any configuration (e.g., strips, bars, segments, etc.) that covers the entirety or any portion of a basin. The heater may be attached to a basin via any conventional or other fastening techniques (e.g., any type of adhesives, brackets, etc.). In addition, the heater may be implemented by any conventional or other type of heater or heating element (e.g., heating coils, etc.) that may be disposed on or proximate a basin at any suitable locations.

The cooling unit may include any conventional or other cooling or refrigeration device and components to control cooling of a basin to any desired temperature (e.g., preferably to temperatures near or below the freezing temperature of the sterile liquid or medium, such as temperatures in the approximate range of −32° F. to 32° F.). The various power switches and controllers of the systems may be implemented by any conventional or other power and control devices and may be disposed on the systems at any suitable locations.

The temperature sensor may be implemented by any quantity of any conventional or other temperature sensing device (e.g., infrared, RTD, etc.), may be disposed at any location on, within or proximate a basin or within the systems to measure temperature of any desired items (e.g., basin, heater or cooler, liquid, etc.). The measured item temperatures may be utilized for display, reports, system operational control or any other desired application. The basins of the systems may be disposed in any arrangement or at any suitable locations on the systems. The systems may thermally treat (e.g., heat or cool) any type of medium or liquid, while a cooling basin may further include any type of conventional or other dislodgement mechanism, such as those described in the aforementioned patents.

The wiring housing may be of any quantity, shape or size, may be constructed of any suitable materials, and may be disposed at any suitable locations on the systems. The wiring housing and/or systems may include any suitable conductors or other medium (e.g., wireless, fiberoptics, etc.) to transfer signals between system components. The wiring housing may include any quantity of any type of receptacle disposed at any suitable location on the wiring housing or systems to interface the drape. The wiring housing may include any quantity of any type of indicator (e.g., audio, speech synthesis, LED, display screen with text or images, speaker, etc.) to indicate the drape container status. The indicator may be disposed on the wiring housing or systems at any suitable locations. The diodes may be of any quantity or color, may be disposed at any suitable locations on the wiring housing or systems and may be illuminated in any desired fashion or pattern (e.g., flashing, continuous illumination, etc.). A drape container or other condition may be associated with any quantity of any diodes of any color (e.g., the same or different colors in any desired combinations, etc.).

The drape may be of any size or shape, and may be constructed of any suitable materials. The drape is preferably transparent or translucent to facilitate manipulation of controls through the drape, however, the drapes may have any degree of transparency (e.g., including opaque). The drape may be manipulated in any fashion with any portions of the drape serving as a drape receptacle within a corresponding basin. The drape may be of sufficient size to accommodate and form drape receptacles within any quantity of thermal treatment system basins.

The drape may include any quantity of electrodes disposed at any suitable locations, whereby each electrode comprises a conductive drape segment and one or more electrical leads connected or coupled in any fashion via any conventional or other coupling techniques. The leads may be constructed of any suitable conductive materials, and may be encased in or include any insulating materials to electrically isolate the leads. The leads may be disposed through the drape at any location or may traverse a drape peripheral or other edge (e.g., without being disposed through the drape) to extend between the sterile and non-sterile drape surfaces. The leads may be sealed in any fashion when disposed through the drape (e.g., formed integral with the drape, material seals, etc.). Drape container conditions may be determined based on any desired electrical or other parameters or characteristics (e.g., potential or voltage, current, resistance, etc.) of any quantity of leads or conductive segments. The parameters may be measured at any suitable locations (e.g., at any locations along each lead or conductive segment, between the leads or conductive segments, between the leads or conductive segments and basin, at the basin, between the leads and detection circuitry, within the detection circuitry, etc.). In addition, the presence of the drape may be detected based on the connection (or lack thereof) of the drape leads to the thermal treatment system (or detection circuitry) to control system operation (e.g., disable thermal treatment of the basin in the absence of a drape, etc.).

The drape may include any quantity of the detection and insulating layers arranged in any fashion. The layers may be of any shape or size, and may be attached or secured together in any fashion. The detection layer may be of any shape or size and be disposed at any location on the drape. For example, the detection layer may be of the size of the basin and indicate the portion of the drape to be placed therein. Further, the layers may be formed as independent drapes and utilized with one covering the other. The insulating and conductive segments may be of any shape or size, and may cover any portion of the detection layer (e.g., the entire layer or any portion thereof, the portion of the layer for placement in a basin, preformed container portion, etc.), where remaining portions of the detection layer (e.g., without the conductive and insulating segments) are typically constructed of insulating materials. The segments may be arranged in any fashion that electrically isolates the conductive segments from each other.

The conductive segments may be constructed of any suitable materials having electrical conductive properties (e.g., conductive metals, conductive polymers (e.g., polyacetylene, polypyrrole, etc.), an electrically conductive carbon filled polymer film, an electrically conductive polymer nanocomposite material, a microporous polymer sheet, a woven or non-woven sheet formed from conductive polymer fibers, a polymeric or other sheet with conductive material deposits, etc.). The insulating segment and layer may be formed of any materials that have minimal or no electrical conducting properties (e.g., insulators, polymeric materials, plastics, etc.). One example of non-conductive drape material is polyolefin. The segment arrangement or detection layer may cover any portion of the insulating layer (e.g., the entire insulating layer or any potion thereof).

The drape may include any quantity of conductive and/or insulating segments for a corresponding basin where signals from the conductive segments may be combined in any fashion (e.g., at least one drape conductive segment detecting liquid, combined logically (e.g., AND, OR, etc.), etc.) to determine occurrence of drape container conditions (e.g., solution or leaks present). The conductive segment plug may be implemented by any conventional or other plug.

The control circuit may be disposed within the systems at any suitable locations and may be implemented by any conventional or other circuitry components arranged in any desired fashion to perform the described functions. The systems may be powered by any conventional or other power source (e.g., AC, DC, wall outlet jack, batteries, etc.). The plugs connecting the power supply or other components may be implemented by any conventional or other connectors for transferring signals. The power cord may be implemented by any conventional or other cord or cable and be configured to accommodate any desired power signals. The thermostat may be implemented by any conventional switching type or limiting devices, such as a high limit thermostat, and may be disposed at any suitable location within the systems.

The detection circuitry may be disposed within the system at any suitable locations and may include any quantity of conventional or other components arranged in any desired fashion to perform the functions described herein. The detection circuitry may utilize any suitable reference potentials to detect solution, leaks or any other conditions. The electrical connections may include any quantity of components (e.g., power cord, fuses, conductors, connectors, power supply, circuit board, diodes, etc.) arranged in any desired fashion, where each component may be implemented by any conventional or other component performing the described function. The temperature controller may be implemented by any conventional or other temperature controller and include any desired devices for entering a temperature (e.g., buttons, keypad, etc.). The temperature controller may control the heater to any desired temperature range, and may utilize any quantity of set points (e.g., maximum and/or minimum, etc.). The basin power switches of the systems may be implemented by any conventional or other switching device, while the fuses may be implemented by any conventional fuse or other limiting device and may be configured for any current or voltage levels.

The circuit board housing the condition circuit may include any quantity of terminals or pins each associated with any desired signals or portion of the condition circuit. The circuit board may include any quantity of indicators disposed at any suitable locations to indicate the occurrence or status of any desired circuit portion or condition. The power supply may be implemented by any conventional or other power supply or source and provide any desired power signals, and may include any type of conventional or other receptacle for receiving any type of plug or connector. The diodes or other indicators may be connected to the circuit board pins in any desired fashion. The circuit board may house the condition circuit and/or any other desired system circuitry. Further, the circuit board may include devices to record any types of information relating to system operation for subsequent retrieval and analysis (e.g., date and time of thermal treatment disablement and enablement, etc.).

The condition circuit may include any quantity of conventional or other components arranged in any desired fashion to perform the functions described herein. The circuit comparators may be implemented by any conventional or other comparators or comparing devices and may utilize any suitable reference potentials to detect solution, leaks or any other conditions. The inverters may be implemented by any conventional or other inverting devices (e.g., logic gates, circuitry, etc.) to invert circuit signals. The logic circuitry and corresponding logic gates may be implemented by any logic gates or combinational logic (e.g., AND, OR, NAND, NOR, XOR, etc.) and/or circuitry (e.g., comparator, inverter, transistors, etc.) arranged in any desired fashion to combine signals to determine the occurrence of any conditions. The logic circuitry comparators may be implemented by any conventional or other comparators or comparing devices and utilize any desired reference potentials. The oscillator may be implemented by any conventional or other timer or oscillating device producing outputs at any desired frequency. The oscillator may drive any type of device (e.g., speaker, speech synthesis, diode, etc.) to indicate the presence of a condition, while the indicator devices may alternatively be driven by any type of circuitry or mechanism. The speaker may be implemented by any conventional or other speaker or audio device and may provide any suitable audio indication (e.g., beep at any suitable periodic interval, continuous audio output, etc.).

The triac may be implemented by any conventional or other triac or relay type device to provide signals to thermal control circuitry for controlling thermal treatment of a basin. The condition circuit may include any conventional or other circuitry (e.g., resistors, capacitors, inductors, diodes, supply and ground potentials, etc.) arranged in any fashion and including any desired electrical characteristic values (e.g., resistance, potential, capacitance, etc.) to facilitate circuit operation. The condition circuit signals may include any desired logic or voltage levels. The optocoupler may be implemented by any conventional or other optocoupler or other circuitry to control the triac to provide signals to the thermal control circuitry.

The plural basin system may include individual thermal control and detection circuitry associated with each basin to monitor drape container conditions and control basin operation. Alternatively, the plural basin system may include common thermal control and detection circuitry to control each basin in response to drape container conditions. The common circuitry may receive signals from each of the electrodes and control the basins individually or collectively in response to the drape container conditions. The common circuitry may process and combine the signals in any fashion (e.g., AND, OR, etc.) to determine conditions for controlling the basins.

The detection circuitry of the systems may alternatively include a microprocessor to process electrode signals and control the indicators, heater or any other devices. In this case, electrode signals are converted to digital signals and compared by the microprocessor to threshold levels for each condition. The microprocessor may generate the appropriate control signals to control basin thermal devices and various indicators in accordance with the determined conditions. The microprocessor may be implemented by or implement the temperature controller and/or report processor.

The control circuitry may include devices to record any types of information relating to system operation for subsequent retrieval, analysis, display and reports (e.g., date and time of thermal treatment disablement and enablement, etc.). The processor may be implemented by any conventional or other microprocessor or controller and include any quantity of any desired input devices (e.g., buttons, keypad, etc.). The processor may maintain the date, elapsed heating time and/or occurrence time of any event or condition (e.g., time when a leak occurs, time instruments inserted within drape container, etc.). The processor may measure the elapsed time or record an occurrence time for any desired condition. The processor may maintain the time information internally or utilize any desired external circuitry (e.g., a timer, etc.).

The processor may collect any desired information (e.g., start date and time of solution heating, the time interval the solution was heated, the temperature the solution attained during heating, partial or complete history of time and solution temperature measured at any desired time intervals, facility name and location, patient information, doctor information, type of procedure, type of solution and/or instruments being heated, amount of solution being heated, etc.) from any desired sources (e.g., detection circuitry, temperature controller, user, memory device, another computer or device, etc.).

The reports may be arranged in any fashion and include any desired information. The report information may be arranged and/or presented (e.g., printed, displayed, etc.) in any desired formats (e.g., text, charts, graphs, etc.). The report and/or information may alternatively be stored in a local or remote database or memory device (e.g., local memory, removable memory, etc.) for later retrieval. The reports may include a pre-arranged format or may be programmable or selected by a user via processor input devices. The system, controller and processor displays may be of any quantity, shape or size, may be disposed at any location on and/or within the system (e.g., cabinet, wiring housing, etc.) or remote from the system, may be implemented by any conventional or other displays (e.g., LED, LCD, etc.) and may display any desired information. The information displayed may be selected via controller or processor input devices, or the display may include display controls (e.g., buttons, keys, etc.).

The printer may be implemented by any conventional or other printing device, may be local or remote, may serve any quantity of systems or other devices, and may produce reports on any desired medium (e.g., paper, labels, etc.). The reports may be printed at any specific time or in response to user entered information (e.g., a print command or key). The printer slot may be of any quantity, shape or size and may be disposed at any suitable location on the cabinet and/or wiring housing. The report may be printed at any desired time before, during or after system use, and may be retrieved from the system at any desired time or in any desired manner that preserves a sterile field (e.g., after completion of the medical procedure, after discarding the drape, times when a sterile field is not needed or being employed by the system, etc.).

The communications module may be implemented by any conventional or other communications device or module (e.g., modem, etc.) and may download or transfer an electronic form of the report to any desired device (e.g., PDA, computer, another thermal treatment or other system, etc.) at any specific time or in response to user entered information (e.g., transmit command or key). The systems may further be networked to enable retrieval of reports and/or information from a station coupled to the network. The printer and communications module may be disposed at any suitable locations on or within the system (e.g., on or within the cabinet, wiring housing, etc.) or remote from the system. Any desired information may be transmitted between the control circuitry components (e.g., temperature controller, detection circuitry, processor, printer, communications module, displays, etc.) via any conventional or other communications medium or protocols (e.g., hardwire, wireless, network, etc.). The processor may implement or be implemented by the temperature controller. The temperature sensor may be coupled to the temperature controller, microprocessor and/or processor either individually or in any combination or fashion.

Software for the temperature controller, detection circuit microprocessor for processing the electrode signals and report processor may be implemented in any desired computer language and could be developed by one of ordinary skill in the computer arts based on the functional descriptions contained herein. The controller, microprocessor and/or processor may alternatively be implemented by any type of hardware and/or other processing circuitry, and may be available pre-programmed for immediate use. The various functions of the controller, microprocessor and/or processor may be distributed in any manner among any quantity of software modules, processors and/or circuitry.

It is to be understood that the terms "top", "bottom", "front", "rear", "side", "height", "length", "width", "upper", "lower" and the like are used herein merely to describe points of reference and do not limit the present invention to any particular orientation or configuration.

The drape is not limited to the applications or systems described above, but may be utilized to facilitate communication or passage of signals or information between the sterile and non-sterile sides of the drape without compromising the sterile field. Further, the conductive segments may be connected to various sensors or any other types of measuring, analytical and/or control devices to measure, determine and/or indicate any types of conditions and/or control system operation in any desired fashion in response thereto.

From the foregoing description, it will be appreciated that the invention makes available a novel surgical drape and method of detecting fluid and leaks in thermal treatment system basins, wherein a surgical drape is constructed of conductive and insulating drape portions or segments to provide signals indicating drape container conditions to a thermal treatment system to facilitate control of system operation.

Having described preferred embodiments of a new and improved surgical drape and method of detecting fluid and leaks in thermal treatment system basins, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for detecting conditions within containers formed by surgical drapes during surgical procedures and controlling thermal treatment of said containers in response to said detected conditions, said system comprising:
   a thermal treatment unit to thermally treat a liquid and including a basin;
   a surgical drape, covering and substantially conforming to said basin, to serve as a drape container for said liquid, wherein a sterile surface of said drape includes a plurality of conductive and insulating drape segments with potentials of said conductive segments being responsive to contact between said conductive segments and said liquid to indicate conditions of said drape container;
   a controller to operate said thermal treatment unit to control a temperature of said basin; and
   a detection unit in communication with said drape to determine occurrence of said drape container conditions from said potentials of said conductive segments and to control said controller to operate said thermal treatment unit in accordance with said determined drape container conditions.

2. The system of claim 1, wherein said drape includes:
   a detection layer including at least said conductive drape segments; and
   an insulating layer attached to said detection layer and placeable proximate said basin to insulate said detection layer from said basin.

3. The system of claim 1, wherein said conductive segments are electrically isolated from each other by at least one insulating segment.

4. The system of claim 3, wherein at least one insulating segment is disposed between adjacent conductive segments to electrically isolate said adjacent conductive segments.

5. The system of claim 1, wherein said drape includes conductors each extending from a corresponding conductive segment to convey signals from said conductive segments to said detection unit.

6. The system of claim 5, wherein said conductors are disposed through said drape to extend between sterile and non-sterile drape surfaces.

7. The system of claim 5, wherein said conductors traverse a drape peripheral edge to extend between sterile and non-sterile drape surfaces.

8. The system of claim 1 further including a plurality of indicators to indicate drape container conditions, wherein said indicators are actuable in response to control signals generated by said detection unit in accordance with said determined occurrence of said drape container conditions.

9. The system of claim 8, wherein at least one indicator includes a visual indicator to visually indicate occurrence of a drape container condition.

10. The system of claim 8, wherein at least one indicator includes an audio indicator to produce audio signals to indicate occurrence of a drape container condition.

11. The system of claim 1, wherein said detection unit disables said thermal treatment unit in response to determining the presence of a leak or absence of said liquid within said drape container.

12. The system of claim 1, wherein said detection unit enables said thermal treatment unit in response to determining the presence of said liquid and absence of a leak within said drape container.

13. The system of claim 1, wherein said drape detects and facilitates indication of conditions of said drape container including the presence of said liquid and a leak within said drape container.

14. The system of claim 1, wherein said thermal treatment unit is operative to cool said liquid in said drape container.

15. The system of claim 1, wherein said thermal treatment unit is operative to heat said liquid in said drape container.

16. The system of claim 1, wherein said drape includes a pre-formed container portion to form said drape container within said basin.

17. The system of claim 1 further including a processor to collect information relating to said liquid and to generate a report including said collected information.

18. The system of claim 17 further including a printer to print a hardcopy of said report.

19. The system of claim 17 further including a communications module to establish communications and transfer information with another device.

20. The system of claim 19, wherein said processor generates said report in electronic form and said communications module transmits said report to said other device.

21. The system of claim 1 further including:
a plurality of said thermal treatment units to thermally treat said liquid and each including a basin, wherein said surgical drape covers and substantially conforms to each said basin to serve as said drape container for said liquid in each said basin, and wherein each drape container includes a plurality of conductive and insulating drape segments with potentials of said conductive segments being responsive to contact between said conductive segments and said liquid to indicate conditions of that drape container;
at least one controller to operate said thermal treatment units to control temperature of each said basin; and
at least one detection unit in communication with each said drape container to determine occurrence of drape container conditions within said each basin from said potentials of said conductive segments associated with that basin to control said at least one controller to operate said thermal treatment units in accordance with said determined drape container conditions.

22. A device for detecting conditions within a basin of a thermal treatment system during surgical procedures and facilitating control of thermal treatment of said basin and liquid contained therein in response to said detected conditions, said device comprising:
a surgical drape to cover and substantially conform to said basin to serve as a drape container for said liquid, wherein a sterile surface of said drape includes a plurality of conductive and insulating drape segments with potentials of said conductive segments being responsive to contact between said conductive segments and said liquid to indicate conditions of said drape container.

23. The device of claim 22, wherein said drape includes:
a detection layer including at least said conductive drape segments; and
an insulating layer attached to said detection layer and placeable proximate said basin to insulate said detection layer from said basin.

24. The device of claim 22, wherein said conductive segments are electrically isolated from each other by at least one insulating segment.

25. The device of claim 24, wherein at least one insulating segment is disposed between adjacent conductive segments to electrically isolate said adjacent conductive segments.

26. The device of claim 22, wherein said drape includes conductors each extending from a corresponding conductive segment to convey signals from said conductive segments to said thermal treatment system.

27. The device of claim 26, wherein said conductors are disposed through said drape to extend between sterile and non-sterile drape surfaces.

28. The device of claim 26, wherein said conductors traverse a drape peripheral edge to extend between sterile and non-sterile drape surfaces.

29. The device of claim 22, wherein said drape detects and facilitates indication of conditions of said drape container including the presence of said liquid and a leak within said drape container.

30. The device of claim 22, wherein said drape includes a pre-formed container portion to form said drape container within said basin.

31. The device of claim 22, wherein:
said thermal treatment system includes a plurality of said basins to thermally treat said liquid; and
said surgical drape covers and substantially conforms to each said basin to serve as said drape container for said liquid in each said basin, and wherein each drape container includes a plurality of conductive and insulating drape segments with potentials of said conductive segments being responsive to contact between said conductive segments and said liquid to indicate conditions of that drape container.

32. A method of detecting conditions during surgical procedures within a container formed within a thermal treatment system basin by a surgical drape to contain liquid and controlling thermal treatment of said drape container in response to said detected conditions, wherein a sterile surface of said drape includes a plurality of conductive and insulating drape segments with potentials of said conductive segments being responsive to contact between said conductive segments and said liquid to indicate conditions of said drape container, said method comprising the steps of:
(a) placing said surgical drape over said thermal treatment system to cover and substantially conform to said basin to serve as a drape container for said liquid;
(b) altering potentials of said conductive segments in response to contact between said conductive segments and said liquid to indicate conditions of said drape container; and
(c) determining occurrence of said drape container conditions from said potentials of said conductive segments and controlling said thermal treatment system to thermally treat said basin in accordance with said determined drape container conditions.

33. The method of claim 32, wherein step (c) further includes:
(c.1) detecting and facilitating indication of said drape container conditions including the presence of said liquid and a leak within said drape container.

34. The method of claim 32, wherein step (c) further includes:
(c.1) actuating at least one of a visual and an audio indicator to indicate said determined occurrence of said drape container conditions.

35. The method of claim 32, wherein step (c) further includes:
(c.1) disabling said thermal treatment system in response to determining the presence of a leak or absence of said liquid within said drape container.

36. The method of claim 32, wherein step (c) further includes:
(c.1) enabling said thermal treatment system in response to determining the presence of said liquid and absence of a leak within said drape container.

37. The method of claim 32 further including:
(d) collecting information relating to said liquid and generating a report including said collected information.
38. The method of claim 37 further including:
(e) printing a hardcopy of said report.
39. The method of claim 37 further including:
(e) establishing communications and transferring information with another device.
40. The method of claim 39, wherein step (e) further includes:
(e.1) generating said report in electronic form and transmitting said report to said other device.
41. The method of claim 32, wherein said thermal treatment system includes a plurality of said basins, and step (a) further includes:
(a.1) placing said surgical drape over said thermal treatment system to cover and substantially conform to each said basin to serve as a drape container for said liquid, wherein said surgical drape covers and substantially conforms to each said basin to serve as said drape container for said liquid in each said basin, and wherein each drape container includes a plurality of conductive and insulating drape segments with potentials of said conductive segments being responsive to contact between said conductive segments and said liquid to indicate conditions of that drape container;
step (b) further includes:
(b.1) altering potentials of said conductive segments of a corresponding drape container in response to contact between those conductive segments and said liquid to indicate conditions of that drape container; and
step (c) further includes:
(c.1) determining occurrence of conditions of each said drape container from said potentials of said conductive segments associated with that drape container and controlling said thermal treatment system to thermally treat said basins in accordance with said determined drape container conditions.
42. A method of detecting conditions within a basin of a thermal treatment system during surgical procedures and facilitating control of thermal treatment of said basin and liquid contained therein in response to said detected conditions, said method comprising the step of:
(a) forming a surgical drape to cover and substantially conform to said basin to serve as a drape container for said liquid, wherein a sterile surface of said drape includes a plurality of conductive and insulating drape segments with potentials of said conductive segments being responsive to contact between said conductive segments and said liquid to indicate conditions of said drape container.

43. The method of claim 42, wherein step (a) further includes:
(a.1) forming said drape to include a detection layer including at least said conductive drape segments and an insulating layer attached to said detection layer and placeable proximate said basin to insulate said detection layer from said basin.
44. The method of claim 42, wherein step (a) further includes:
(a.1) electrically isolating said conductive segments from each other via at least one insulating segment.
45. The method of claim 44, wherein step (a.1) further includes:
(a.1.1) disposing at least one insulating segment between adjacent conductive segments to electrically isolate said adjacent conductive segments.
46. The method of claim 42 further including:
(b) attaching conductors to said drape, wherein said conductors each extend from a corresponding conductive segment to convey signals from said conductive segments to said thermal treatment system.
47. The method of claim 46, wherein step (b) further includes:
(b.1) disposing said conductors through said drape to extend between sterile and non-sterile drape surfaces.
48. The method of claim 46, wherein step (b) further includes:
(b.1) attaching said conductors to said drape, wherein said conductors traverse a drape peripheral edge to extend between sterile and non-sterile drape surfaces.
49. The method of claim 42 further including:
(b) detecting and facilitating indication of conditions of said drape container including the presence of said liquid and a leak within said drape container.
50. The method of claim 42, wherein step (a) further includes:
(a.1) forming said drape to include a pre-formed container portion to form said drape container within said basin.
51. The method of claim 42, wherein said thermal treatment system includes a plurality of said basins to thermally treat said liquid, and step (a) further includes:
(a.1) forming said drape to cover and substantially conform to each said basin to serve as said drape container for said liquid in each said basin, wherein each drape container includes a plurality of conductive and insulating drape segments with potentials of said conductive segments being responsive to contact between said conductive segments and said liquid to indicate conditions of that drape container.

* * * * *